United States Patent
Greener

(10) Patent No.: US 12,070,544 B2
(45) Date of Patent: *Aug. 27, 2024

(54) NEGATIVE PRESSURE DEVICE

(71) Applicant: Smith & Nephew PLC, Watford (GB)

(72) Inventor: Bryan Greener, York (GB)

(73) Assignee: Smith & Nephew PLC, Watford (GB)

( * ) Notice: Subject to any disclaimer, the term of this patent is extended or adjusted under 35 U.S.C. 154(b) by 527 days.

This patent is subject to a terminal disclaimer.

(21) Appl. No.: 16/234,257

(22) Filed: Dec. 27, 2018

(65) Prior Publication Data

US 2019/0240381 A1 Aug. 8, 2019

Related U.S. Application Data

(63) Continuation of application No. 13/824,967, filed as application No. PCT/GB2011/051748 on Sep. 16, 2011, now Pat. No. 10,188,776.

(30) Foreign Application Priority Data

Sep. 20, 2010 (GB) .................................... 1015709
Sep. 20, 2010 (GB) .................................... 1015710

(51) Int. Cl.
*A61M 1/00* (2006.01)

(52) U.S. Cl.
CPC ............... *A61M 1/743* (2021.05); *A61M 1/60* (2021.05); *A61M 1/74* (2021.05); *A61M 1/96* (2021.05)

(58) Field of Classification Search
CPC ........ A61M 1/00; A61M 27/00; A61M 1/743; A61M 1/0003; A61M 1/60; A61M 1/74; A61M 1/96; A61F 13/00; A61F 13/02
(Continued)

(56) References Cited

U.S. PATENT DOCUMENTS 5,215,539 A 6/1993 Schoolman
5,248,275 A * 9/1993 McGrath ................. B29C 65/18
  137/844
(Continued)

FOREIGN PATENT DOCUMENTS

DE 4012232 A1 10/1991
GB 2378392 A 2/2003
(Continued)

OTHER PUBLICATIONS

Australian Office Action, re AU Application No. 2011306735, dated Dec. 19, 2013.
(Continued)

*Primary Examiner* — Andrew J Mensh
(74) *Attorney, Agent, or Firm* — Knobbe, Martens, Olson & Bear, LLP

(57) ABSTRACT

A method and apparatus are disclosed for providing negative pressure at a wound site. The apparatus includes a suction pump for generating negative pressure, a negative pressure reservoir, a valve element arranged to selectively provide a fluid communication path between the reservoir and the wound site while a negative pressure in the negative pressure reservoir is greater than a threshold negative pressure, to thereby provide a desired negative pressure at the wound site, and wherein in response to a pressure in the negative pressure reservoir decreasing to the threshold negative pressure, the suction pump is operable to re-establish an initial negative pressure in the negative pressure reservoir.

13 Claims, 18 Drawing Sheets

(58) Field of Classification Search
USPC .......................................................... 604/320
See application file for complete search history.

(56) References Cited

U.S. PATENT DOCUMENTS

| | | | |
|---|---|---|---|
| 5,813,842 A * | 9/1998 | Tamari | F16K 7/07 |
| | | | 417/63 |
| 6,196,519 B1 * | 3/2001 | Utterberg | A61M 39/284 |
| | | | 251/9 |
| 6,458,109 B1 | 10/2002 | Henley et al. | |
| 6,471,679 B1 | 10/2002 | Suh | |
| 6,588,613 B1 * | 7/2003 | Pechenik | A61J 11/001 |
| | | | 215/11.1 |
| 7,700,819 B2 | 4/2010 | Ambrosio et al. | |
| 7,790,946 B2 | 9/2010 | Mulligan | |
| 8,323,264 B2 | 12/2012 | Weston et al. | |
| 8,372,049 B2 | 2/2013 | Jaeb et al. | |
| 8,382,731 B2 | 2/2013 | Johannison | |
| 8,785,059 B2 | 7/2014 | Hartwell | |
| 8,808,259 B2 | 8/2014 | Walton et al. | |
| 8,843,327 B2 | 9/2014 | Vernon-Harcourt et al. | |
| 8,852,170 B2 | 10/2014 | Weston et al. | |
| 8,864,748 B2 | 10/2014 | Coulthard et al. | |
| 10,188,776 B2 * | 1/2019 | Greener | A61M 1/60 |
| 2005/0261642 A1 | 11/2005 | Weston | |
| 2007/0225663 A1 | 9/2007 | Watt et al. | |
| 2009/0030383 A1 * | 1/2009 | Larsen | A61M 1/743 |
| | | | 604/315 |
| 2010/0274229 A1 * | 10/2010 | Duocastella Codina | |
| | | | A61M 1/684 |
| | | | 604/317 |
| 2011/0172615 A2 | 7/2011 | Greener | |
| 2011/0275964 A1 | 11/2011 | Greener | |
| 2013/0296816 A1 | 11/2013 | Greener | |
| 2014/0188061 A1 | 7/2014 | Locke et al. | |
| 2014/0236109 A1 | 8/2014 | Greener | |

FOREIGN PATENT DOCUMENTS

| | | |
|---|---|---|
| JP | 2002-291869 | 10/2002 |
| JP | 4939407 B2 * | 6/2004 |
| WO | WO 1993/18324 | 9/1993 |
| WO | WO-2004037334 A1 | 5/2004 |
| WO | WO-2007051599 A1 | 5/2007 |
| WO | WO 2014/043225 | 3/2014 |

OTHER PUBLICATIONS

Chinese Office Action re CN Application No. 201180055766.4, issued Jan. 30, 2015.
Chinese Office Action, re CN Application No. 201180055766.4, issued Dec. 22, 2015.
Chinese Office Action, re CN Application No. 201180055766.4, issued Aug. 31, 2016.
European Office Action, re EP Application No. 16 194 965.6, dated Feb. 17, 2017.
International Search Report, re PCT Application No. PCT/GB2011/051748, mailed Apr. 2, 2012.
International Search Report, re PCT Application No. PCT/GB2011/051748, dated Apr. 2, 2012.
Japanese Office Action, re JP Application No. 2013-528769, mailed Jul. 27, 2015.
Japanese Office Action, re JP Application No. 2016-013113, mailed Dec. 19, 2016.
Mexican Office Action, re MX App. No. MX/a/2013/003091, dated Apr. 24, 2015.
Mexican Office Action, re MX Application No. MX/a/2013/003091, dated Nov. 23, 2015.
Mexican Office Action, re MX Application No. MX/a/2013/003091, dated Jun. 30, 2016.
Russian Office Action, re RU Application No. 2013117738/14, dated Aug. 26, 2015.
Russian Office Action, re RU Application No. 2013117738/14, dated Dec. 10, 2015.
Brief communication—Opposition proceedings to patent proprietor for European Patent No. 3202430, dated Nov. 2, 2020, 4 pages.
Brief Communication of the letter from the proprietor—Request for change of applicant's representative and letter requesting extension for European Patent No. 3202430, dated Oct. 20, 2020, 6 pages.
Communication Indicating Deficiencies in the Notice of Opposition, re the Opposition of European Patent No. 3202430, dated Apr. 29, 2020, 2 pages.
International Preliminary Report on Patentability for Application No. PCT/GB2011/051748, mailed on Apr. 4, 2013, 12 pages.
Letter regarding the Opposition Procedure, re the Opposition of European Patent No. 3202430, dated May 4, 2020, 5 pages.
Notice of Opposition—Statement of Facts and Evidence, *Lohmann & Rauscher GmbH* vs. *Smith & Nephew PLC*, re European Patent No. 3202430, dated Apr. 17, 2020, 26 pages.
Opposition procedure—Extension of time limit pursuant to Rule 132 EPC for European Patent No. 3202430, dated Oct. 29, 2020, 1 page.
Priority Document filed Sep. 20, 2010 for Great Britain Application No. 1015709.7, by Smith & Nephew PLC, 23 pages.
Priority Document filed Sep. 20, 2010 for Great Britain Application No. 1015710.5, by Smith & Nephew PLC, 28 pages.
Specification and drawings as filed in EP Application No. 16194965.6 on Sep. 16, 2011, by Smith & Nephew PLC, 65 pages.
Written Opinion for Application No. PCT/GB2011/051748, mailed on Apr. 2, 2012, 10 pages.
Brief Communication—Letter from the Opponent for Opposition against the European Patent No. 3202430, mailed on Mar. 12, 2021, 33 pages.
Reply of the Patent Proprietor to the Notice(s) of Opposition for European Patent No. 3202430, dated Jan. 8, 2021, 11 pages.
Notice of Opposition—Statement of Facts and Evidence, *Lohmann & Rauscher GmbH* vs. *Smith & Nephew PLC*, re European Patent No. 3202430, dated Apr. 17, 2020, with English translation, 45 pages.
Beswick Engineering Co., Inc., "Diaphragm Vacuum Regulator has Ultra-Miniature Design," Pressure Regulators, Mar. 15, 2005, 4 pages.
Laboratory, "Miniature Single-Stage Diaphragm Vacuum Regulator," Laboratory Talk press release, Feb. 25, 2005, 2 pages.
Opponent's Written Submission in Preparation for the Oral Proceedings for the Opposition of European Patent No. 3202430, dated Sep. 29, 2021, 15 pages.
Opponent's Written Submission in Preparation for the Oral Proceedings, the Opposition of European Patent No. 3202430, dated Sep. 21, 2021, 3 pages.
Proprietor's Written Submission in Preparation for the Oral Proceedings for the Opposition of European Patent No. 3202430, dated Sep. 29, 2021, 15 pages.
Information about the Result of Oral Proceedings, the Opposition of European Patent No. 3202430, dated Nov. 29, 2021, 4 pages.
Interlocutory Decision in Opposition proceedings for European Patent No. 3202430, mailed on Dec. 13, 2021, 71 pages.
Notice of Appeal for European Patent No. 3202430, mailed on Jan. 28, 2022, 4 pages.
Statement of Grounds of Appeal for the European Patent No. 3202430, mailed on Apr. 8, 2022, 70 pages.
Board of Appeal—Letter of the Patent Proprietor dated Aug. 16, 2022, for European Patent No. 3202430, mailed on Aug. 22, 2022, 11 pages.
Board of Appeal—Letter of the Opponent O2 dated Dec. 5, 2022 for European Patent No. 3202430, mailed on Dec. 8, 2022, 23 pages.
Letter relating to the Appeal Procedure for the Opposition of the European Patent No. 3202430, mailed on Apr. 25, 2023, 4 pages.
Consolidated List of Cited Opposition Documents, re European Patent No. EP 3 202 430 dated Mar. 26, 2020, in 1 page.
Notice of Opposition—Statement of Facts and Evidence, re European Patent No. EP 3 202 430, dated Mar. 24, 2020, in 20 pages.

* cited by examiner

NEGATIVE PRESSURE DEVICE

CROSS-REFERENCE TO RELATED APPLICATIONS

This application is a continuation of U.S. application Ser. No. 13/824,967, filed Jul. 15, 2013, which is a U.S. National Phase of PCT International Application No. PCT/GB2011/051748, filed on Sep. 16, 2011, designating the United States and published on Mar. 29, 2012 as WO 2012/038727, which claims priority to Great Britain Patent Application No. 1015710.5, filed on Sep. 20, 2010 and to Great Britain Patent Application No. 1015709.7, filed on Sep. 20, 2010. The disclosure of all three of the above-referenced applications are incorporated by reference herein in their entireties and should be considered a part of this application.

BACKGROUND OF THE DISCLOSURE

Field of the Disclosure

The present invention relates to an apparatus and method for providing negative pressure at a wound site. In particular, but not exclusively, the present invention relates to an apparatus including a negative pressure reservoir able to continually or repeatedly "top up" an applied negative pressure so that negative pressure applied at a wound site can be maintained within desired limits for a relatively long period of time without operation of a powered source of negative pressure. The present invention also relates to an apparatus and method for selectively providing a fluid communication path. In particular, but not exclusively, the present invention relates to an apparatus for connecting two chambers containing negative pressures and capable of regulating the communication of negative pressure between the two chambers.

Background

Devices for the generation of negative pressure at the surface of skin have been used for many hundreds of years to treat animal and human bodies. For example the cupping technique (which relates to the positioning of a mouth of a rigid vessel containing hot air) is a well known technique. Spring powered syringes and suction cups are other mechanical techniques which have been used in the past for generating a vacuum on tissue. In common with cupping such techniques have, in the past, suffered from a very limited longevity of the therapy which can be applied. That is to say the duration of the negative pressure which can be maintained over a site of application has been limited.

To enable a more prolonged application of controlled negative pressure, powered systems, which include a vacuum generation source such as a pump of some type, have been developed and many examples of such systems are used today for the management of wounds. However, many of these systems are not convenient for discreet use by a patient as they are large, can be heavy and are often noisy.

Furthermore, such systems rely on continuous connection of the patient to the vacuum generation source. Disconnection from the vacuum generation source may be possible for short periods, but such periods should be minimized as prolonged disconnection can increase the risk of dressing failure and of ingress of contaminants into the wound (including bacteria).

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus. To this end GB-A-2 307 180, which is herein incorporated by reference, describes a portable TNP therapy unit which may be carried by a patient and clipped to belt or harness. A negative pressure can thus be applied at a wound site. However, the described portable TNP apparatus still relies on a continuous connection of the wound site to a powered vacuum source to provide the negative pressure at the wound site.

In order to maintain the negative pressure at the wound site, the vacuum generator, commonly a pump, operates at a frequency dictated by fluid (exudate or gas) ingress into the system during its operation. Fluid ingress rates may be at a level that results in the pump running unpredictably every few minutes or tens of minutes. The powered vacuum source, or pump, creates noise, vibration and heat.

The intermittent operation of a pump and its associated valving creates a level of noise and vibration that is difficult to perceive in a working environment (office, hospital) but becomes all too obvious in the home, particularly when attempting to sleep. Noise levels in working environments (including air conditioning units and other electronic equipment) are frequently above 50 dB while those in the home, during the night, are frequently less than 20 dB.

The noise and vibration levels created by the unpredictable and intermittent operation of the powered pump in current NPWT systems is frequently unacceptable for home use and negatively impacts quality of life of the patient.

Pressure regulators can be used to control the communication of pressure between an inlet and an outlet, in order to provide a desired stable pressure level. For example, there exist certain medical applications in which it is desirable to apply a negative pressure to a body location, however the level of negative pressure provided by a vacuum pump may be excessive and a regulator may be used to control the negative pressure communicated to the application site.

In International Patent Application, WO 96/11031, a method and apparatus for draining a closed wound employing sub-atmospheric pressure is described. A regulator valve is described that is able to regulate the applied sub-atmospheric, or negative pressure, to the closed wound. The regulator valve is controllable to allow a desired negative pressure to be set by a user.

When used for medical applications, the regulator cannot be reused due to the possibility of contamination by the drained wound fluids, and therefore must be single use. Current regulator valves such as that described in WO 96/11031 are relatively complex and therefore the cost of disposing of the regulator after a single use can be significant.

SUMMARY OF SOME EXEMPLIFYING EMBODIMENTS

It is an aim of the present invention to at least partly mitigate the above-mentioned problems.

It is an aim of certain embodiments of the present invention to provide an apparatus which can provide a negative pressure at a wound site for an extended period without requiring the operation of a powered source of negative pressure. This enables a user to sleep undisturbed.

It is an aim of certain embodiments of the present invention to provide a system for decoupling the operation of a powered source of negative pressure from a level of hysteresis specified for a wound site.

It is an aim of certain embodiments of the present invention to provide an apparatus for reliably regulating the communication of negative pressure between an inlet and an outlet that has a simple construction and is of reduced cost.

According to the present invention, there is provided apparatus for providing negative pressure at a wound site, comprising:

a suction pump for generating negative pressure;

a negative pressure reservoir;

a valve element arranged to selectively provide a fluid communication path between the reservoir and the wound site while a negative pressure in the negative pressure reservoir is greater than a threshold negative pressure, to thereby provide a desired negative pressure at the wound site; and wherein in response to a pressure in the negative pressure reservoir decreasing to the threshold negative pressure, the suction pump is operable to re-establish an initial negative pressure in the negative pressure reservoir.

According to the present invention, there is provided a method of providing negative pressure at a wound site, comprising the steps of:

while a negative pressure in a negative pressure reservoir is greater than a threshold negative pressure, selectively providing a fluid communication path between the negative pressure reservoir and the wound site via a valve element to provide a desired negative pressure at the wound site; and in response to the negative pressure in the negative pressure reservoir decreasing to the threshold negative pressure, re-establishing the initial negative pressure in the negative pressure reservoir via a suction pump.

According to the present invention, there is provided a method of limiting runtime of a suction pump for providing negative pressure at a wound site, the method comprising:

via the suction pump, providing an initial negative pressure in a negative pressure reservoir;

selectively providing a fluid communication path between the reservoir and the wound site to provide a desired negative pressure at the wound site; wherein the suction pump is only run when a negative pressure in the negative pressure reservoir is depleted to a threshold negative pressure.

According to the present invention, there is provided apparatus for selectively providing a fluid communication path comprising:

a channel element comprising opposed sidewall elements locatable in an open spaced apart configuration in which a channel is provided between the sidewall elements and in a closed configuration in which the sidewall elements abut to close the channel; wherein the sidewall elements are resilient and are moveable to said open configuration in which the channel provides a fluid communication path or said closed configuration responsive to a pressure difference at the sidewall elements.

According to the present invention, there is provided a method of selectively providing a fluid communication path between first and second zones of negative pressure, the method comprising:

coupling a channel element between a first zone of negative pressure and a second zone of negative pressure, wherein the channel element comprises opposed sidewall elements locatable in an open spaced apart configuration and in a closed configuration wherein the sidewall elements abut to close the channel, wherein the sidewall elements are resilient; and via a pressure difference acting on the resilient sidewall elements, moving the resilient sidewall elements between said open configuration in which the channel provides a fluid communication path between the first and second zones of negative pressure and said closed configuration responsive to the pressure difference.

According to of the present invention, there is provided a method of manufacturing a channel element for selectively providing a fluid communication path, the method comprising:

overlying a masking strip on a first surface of a first sidewall element, the masking strip defining a channel region;

forming a second sidewall element overlying the first surface of the first sidewall element and the masking strip such that in areas of the first surface where the masking strip is absent the first and second sidewall elements are bonded together; and removing the masking strip from in-between the first and second sidewall elements, said first and second sidewall elements comprising said channel element.

According to another aspect of the present invention, a method of limiting runtime of a suction pump for providing negative pressure at a wound site is provided, the method comprising:

via the suction pump, providing an initial negative pressure in a negative pressure reservoir; and selectively providing a fluid communication path between the reservoir and the wound site to provide a desired negative pressure at the wound site, wherein the suction pump is only run when the negative pressure in the negative pressure reservoir is depleted to a first threshold negative pressure; and wherein selectively providing the fluid communication path comprises:

coupling a channel element between a first zone of negative pressure and a second zone of negative pressure, wherein the channel element comprises opposed sidewall elements locatable in an open spaced apart configuration and in a closed configuration wherein the sidewall elements abut to close the channel, wherein the sidewall elements are resilient; and via a pressure difference acting on the resilient sidewall elements, moving the resilient sidewall elements between said open configuration in which the channel provides a fluid communication path between the first and second zones of negative pressure and said closed configuration responsive to the pressure difference.

According to another aspect of the present invention, a method of providing negative pressure at a wound site is provided, the method comprising:

while a negative pressure in a negative pressure reservoir is greater than a first threshold negative pressure, selectively providing a fluid communication path between the negative pressure reservoir and the wound site via a valve element to provide a desired negative pressure at the wound site; and in response to the negative pressure in the negative pressure reservoir decreasing to the first threshold negative pressure, re-establishing the initial negative pressure in the negative pressure reservoir via a suction pump, wherein selectively providing the fluid communication path comprises:

coupling the valve element between a first zone of negative pressure and a second zone of negative pressure, wherein the valve element comprises opposed sidewall elements locatable in an open spaced apart configuration and in a closed configuration wherein the sidewall elements abut to close the channel, wherein the sidewall elements are resilient; and via a pressure difference acting on the resilient sidewall elements, moving the resilient sidewall elements between said open configuration in which the channel provides a fluid communication path between the first and second zones of negative pressure and said closed configuration responsive to the pressure difference.

In some embodiments, the methods further comprise:

placing a wound dressing over a wound or wound site, the wound dressing forming a substantially fluid tight seal over the wound or wound site; and connecting the negative pressure reservoir to the wound dressing.

In some embodiments, providing the desired negative pressure at the wound site from the negative pressure reservoir is accomplished without requiring the operation of a powered source of negative pressure, activating the suction pump, activating a motor, causing a membrane or diaphragm to move, or the like.

In some embodiments, moving the resilient sidewall elements further comprises moving the resilient sidewall elements between a partially open configuration and a closed configuration.

In some embodiments, providing the pressure difference comprises:

applying a negative pressure at the second zone of negative pressure to be communicated to the first zone of negative pressure via the channel or valve element, wherein the negative pressure in the second zone of negative pressure is greater than the negative pressure in the first zone of negative pressure; and wherein the sidewall elements are urged together to close the fluid communication path if the negative pressures in the first and second zones of negative pressure are greater than a second threshold pressure.

In some embodiments, the first zone of negative pressure comprises the wound site and the second zone of negative pressure comprises the negative pressure reservoir.

In some embodiments, the first zone of negative pressure comprises the negative pressure reservoir and the second zone of negative pressure comprises the wound site.

Certain embodiments of the present invention enable the decoupling of narrow hysteresis limits from the operation of a powered source of negative pressure when applying negative pressure at a wound site. Thus, the applied negative pressure can be maintained within narrow hysteresis limits without requiring constant or very frequent operation of a pump.

Certain embodiments of the present invention provide the advantage of allowing negative pressure applied to a wound site to be maintained within hysteresis limits for a prolonged silent period in which a powered source of negative pressure is not operated.

BRIEF DESCRIPTION OF THE DRAWINGS

Certain embodiments of the present invention provide the advantage of a simple and cheap disposable valve element that can be used to regulate the communication of negative pressure according to a design threshold pressure.

Embodiments of the present invention will now be described hereinafter, by way of example only, with reference to the accompanying drawings in which:

FIGS. 11 and 12 illustrate the manufacturing process of a deformable tube valve in which FIG. 11 illustrates the tube before deformation.

In the drawings like reference numerals refer to like parts.

DETAILED DESCRIPTION OF SOME EXEMPLIFYING EMBODIMENTS

Figure 1:
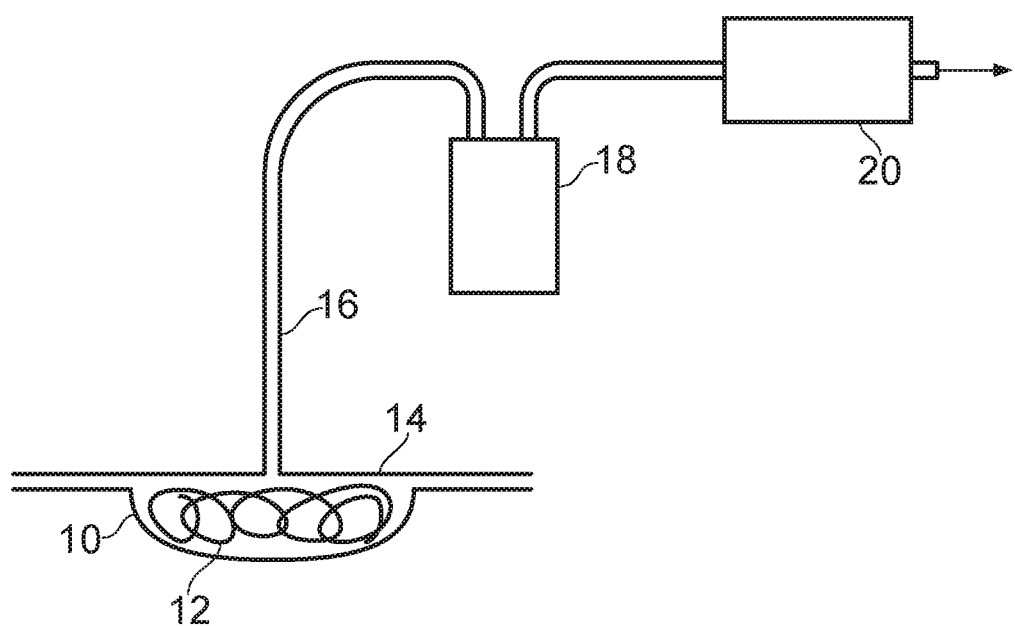
FIG. 1 illustrates a prior art arrangement for applying negative pressure to a wound site.

FIG. 1 illustrates a prior art arrangement for applying negative pressure wound therapy to a wound site 10. A packing material 12 is placed within a wound cavity, and then a drape 14 sealed to the surface of the skin around the wound site 10 forming a fluid tight seal around the perimeter of a wound chamber. A source of negative pressure, such as a pump 20 is coupled to the wound cavity via a tube 16. A fluid collection canister 18 is coupled between the pump 20 and the wound chamber to collect any wound exudate drawn from the wound site 10. The use of the packing material 12 such as a foam, gauze or the like is optional, and it may be omitted in certain arrangements as appropriate.

Also whilst embodiments of the present invention will be described hereinafter by way of reference to a wound chamber defined at a wound site under a drape it will be understood that certain embodiments of the present invention can be utilised to maintain a negative pressure in a wound chamber which is a rigid structure or partly rigid structure such as a cup device placed over a wound site.

In operation, the pump 20 operates to generate a negative pressure in the fluid collection canister 18 and the wound chamber to thereby apply a desired negative pressure to the wound site 10. Over time, small leakage paths will form that allow fluid to leak into the wound chamber. Ingress of fluid such as wound exudate or gas (such as air from the environment) into the wound chamber will lead to the negative pressure at the wound site slowly degrading, i.e. the pressure becoming less negative. Once the pressure degrades to a certain level, the pump 20 operates to re-establish the desired negative pressure at the wound site 10.

The quiet period between pump-operations is defined by both fluid ingress rate and a level of vacuum hysteresis specified by the pump control system. It will be understood by the skilled man that a control system running with 10% hysteresis means that a system initially attains a vacuum level V and this level decays to 90% of its original level before being replenished by the vacuum source. Quiet periods are prolonged in direct proportion to the percentage of hysteresis that is tolerable in the system. A system with 100% hysteresis will be replenished 100-times less frequently than a system with 1% hysteresis. Commonly, in current systems, hysteresis is minimized to below 10% of the target vacuum level because it is believed that this specificity is therapeutic.

Thus, in the arrangement of FIG. 1, the pump 20 operates to re-establish the desired negative pressure depending on the hysteresis level defined for the system. This leads to regular operation of the pump to maintain the desired negative pressure at the wound site 10.

The pump to produce the high vacuum reservoir may be a mechanical or manual pump. The advantage of using a high vacuum reservoir is that the period between top ups of negative pressure is increased, thus reducing the inconvenience to the user.

According to embodiments of the present invention as discussed further below, the operation of a pump to provide negative pressure is decoupled from the level of hysteresis defined for the system, in order to allow the desired negative pressure to be maintained within hysteresis limits for an extended period of time in which the pump does not operate.

This is achieved by the provision of a high vacuum, or negative pressure, reservoir coupled between the pump and the wound site, wherein the high vacuum reservoir is able to store a negative pressure that is greater, i.e. more negative, than the desired negative pressure to be applied at the wound site. The reservoir provides a storage system for vacuum that requires periodic replenishment on a time scale that is of longer duration than that on which the vacuum level at the wound site requires replenishment.

The high vacuum reservoir is connected to the wound site via a vacuum regulation valve that opens when the negative pressure at the wound site falls to a preset minimum level and closes when an initial negative pressure at the wound site is replenished by the high vacuum reservoir.

Figure 2:
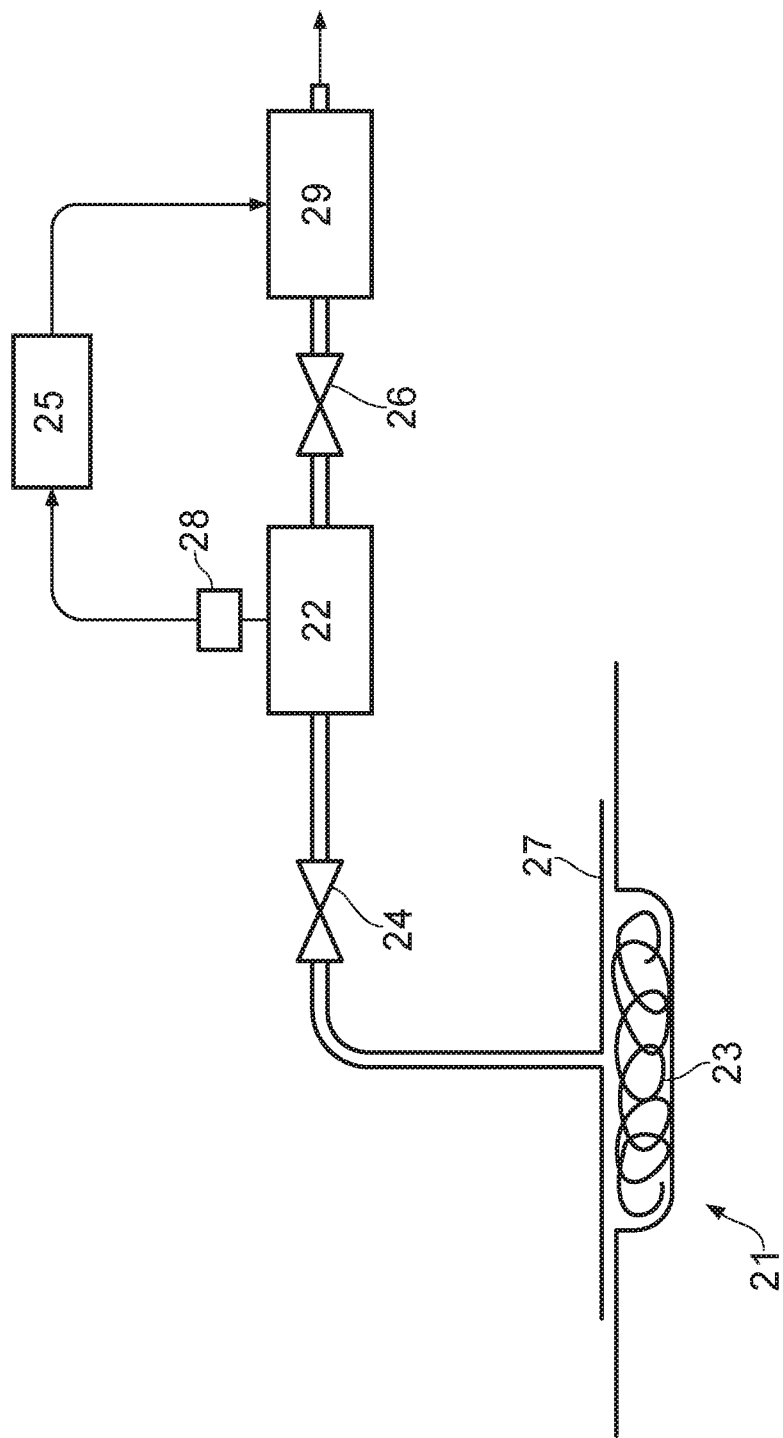
FIG. 2 illustrates an arrangement including a vacuum reservoir for applying negative pressure to a wound site.

FIG. 2 illustrates an arrangement including a high vacuum reservoir for applying negative pressure wound therapy at a wound site 21. As for the embodiment of FIG. 1, packing material 23, such as foam, gauze or the like, may be placed within the wound cavity, and then a drape 27 is sealed to the surface of the skin around the wound site 21 forming a fluid tight seal around the perimeter of the wound chamber.

A vacuum source, such as a pump, 29 is connected to a negative pressure reservoir 22 via a top-up valve 26, to allow the vacuum source 29 to evacuate the system to the desired level of vacuum. The vacuum reservoir 22 is connected to the wound site 21 via reservoir valve 24 which selectively couples the reservoir 22 to the wound site 21 to replenish the negative pressure at the wound site. A pressure sensor 28 is coupled to the negative pressure reservoir 22 and provides a measured pressure value to a control unit 25. The control unit 25 is coupled to the pump 29, and provides control signals to control the operation of the pump. In practice all of these elements may be contained within a single housing, as is traditional currently.

Optionally, the wound chamber may be connected to the reservoir valve 24 via a fluid collection chamber (not shown). Such a collection chamber may include a liquid filter at an outlet thereof which will prevent flow of liquid out of the canister. In this way, the operation of the reservoir valve cannot be compromised by wound exudate containing particulates. Alternatively, the vacuum reservoir 22 may act as a fluid collection canister.

In operation, a wound chamber is assembled in place over the site of application and connected to the vacuum source 29. The high vacuum reservoir 22, as well as the reservoir valve 24 and top-up valve 26, is positioned between the vacuum source 29 and the wound site 21. The vacuum pump 29 is activated and the system is evacuated to the desired value for the wound site 21 (for example 80-125 mmHg below ambient atmospheric pressure). The reservoir valve 24 separating the wound site 21 from the vacuum reservoir 22 closes once the desired negative pressure value is reached and the pump 29 continues to evacuate the remainder of the system. The pump 29 continues to operate until a target level of negative pressure has been established in the vacuum reservoir 22 (for example 200-800 mmHg below ambient atmospheric pressure).

Once the pressure measured by the pressure sensor 28 indicates that the target level of negative pressure has been established, the control unit deactivates the pump 29. The control unit 25 continues to monitor the pressure in the negative pressure reservoir 22 and when the level of negative pressure in the vacuum reservoir 22 drops to a threshold negative pressure, the pump is activated and operates until the target level of negative pressure has been re-established in the vacuum reservoir 22.

Thus, a high level of negative pressure is provided in the vacuum reservoir 22 which is then used to replenish the negative pressure at the wound site 21, without requiring operation of the pump 29. The wound chamber is selectively connected to the vacuum reservoir 22 by the reservoir valve 24 in order to maintain the negative pressure at the wound site within defined limits, according to the desired level of hysteresis. Operation of the pump 29 is only required when the level of negative pressure in the vacuum reservoir drops below a certain threshold level.

The threshold negative pressure level may, for example, be equal to the desired negative pressure at the wound site 21. Once the pressure in the vacuum reservoir 22 degrades to the desired negative pressure, it will no longer be possible for the pressure at the wound site to be replenished to the desired level by coupling the wound chamber to the vacuum reservoir 22, and so the negative pressure in the reservoir 22 must be replenished using the pump 29.

As an alternative logic could be provided in the control unit 25 such that if a measured pressure in the reservoir is <−2V (assuming an equal approximate volume in the reservoir and wound chamber) then the valve 26 opens on the next instance that the pressure in the wound chamber falls to a predetermined target value, for example 0V or the like.

It will be understood that the volume of and the vacuum level contained within the high vacuum reservoir 22 and the volume of and the vacuum level contained within the wound chamber formed over the wound site 21 and the level of hysteresis of the reservoir valve 26 are all directly related to the relative replenishment period of the high vacuum reservoir 22.

To understand the effect of the relationship between the relative volumes of the high vacuum reservoir and the wound chamber on the period of high vacuum reservoir replenishment, consider a system with a vacuum reservoir having equal volume to the wound chamber and running 100% hysteresis in the wound contact chamber. Let the initial vacuum in the vacuum reservoir be −5V and the vacuum in the wound contact chamber be −1V. Fluid ingress occurs and the vacuum in the wound contact chamber falls to atmospheric pressure (0V). The connecting reservoir valve 24 opens and the high vacuum reservoir 22 replenishes the wound contact chamber to −1V, leaving −4V remaining in the reservoir chamber 22. Further fluid ingress then occurs and the process repeats leaving −3V, −2V and finally −1V remaining in the vacuum reservoir 22. At this point, it will not be possible to replenish the negative pressure at the wound site a further time to the −1V level by coupling the wound site to the vacuum reservoir 22, and the negative pressure in the vacuum reservoir 22 should be replenished. In this arrangement, the high vacuum reservoir 22, of equal volume to the wound chamber, but at five-times higher vacuum, extends the quiet period in between replenishment of the high vacuum reservoir by five-fold compared to the same system in the absence of a high vacuum reservoir.

Figure 3:
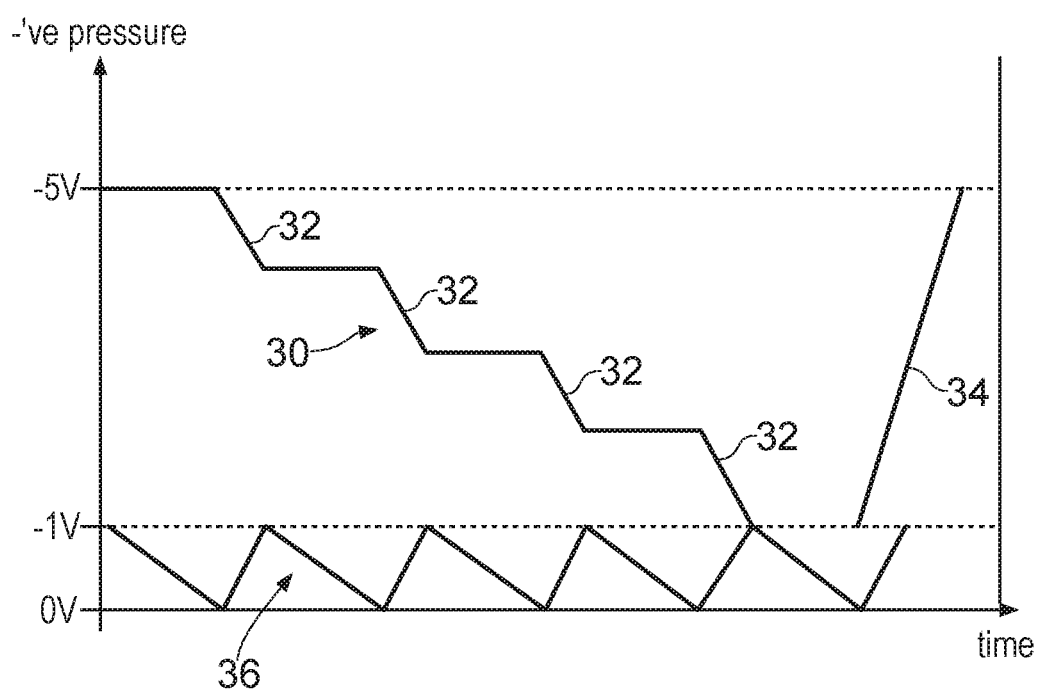
FIG. 3 illustrates negative pressure levels during operation of the arrangement of FIG. 2.
Figure 4:
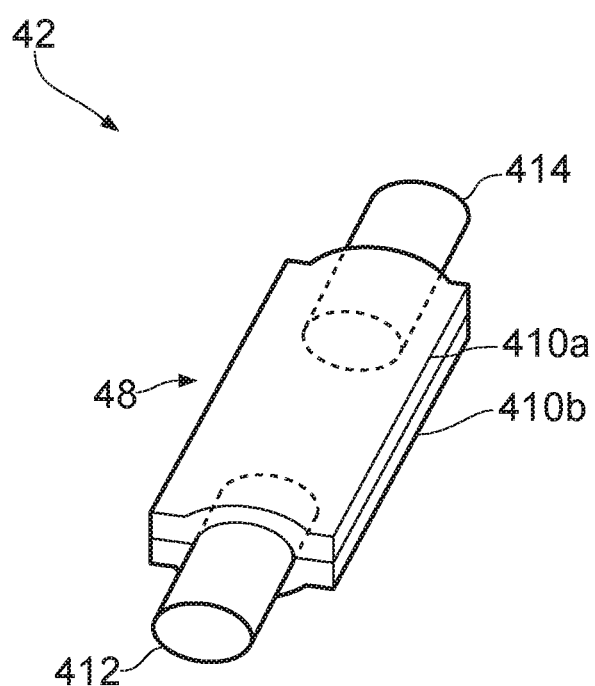
FIG. 4 illustrates a valve element.

FIG. 3 shows a graph of the vacuum reservoir pressure 30 and the wound site pressure 36 for the above described example. The pressure 30 in the negative pressure reservoir is initially −5V and the pressure 36 at the wound site is initially −1V. The pressure at the wound site slowly degrades due to fluid ingress and eventually falls to atmospheric pressure. At this point the reservoir valve 24 opens and the negative pressure in the vacuum reservoir 22 is used to replenish the negative pressure at the wound site. This can be seen by the drop in pressure 32 in the negative pressure reservoir. This cycle repeats a further three times until the pressure in the negative pressure reservoir reaches −1V. When the pressure at the wound site next falls to atmospheric pressure, there is no longer sufficient negative pressure in the vacuum reservoir 22 to replenish the negative pressure at the wound site, and the pump 20 operates to replenish the negative pressure in the negative pressure reservoir resulting in a rise in pressure 34 in the negative pressure reservoir.

Now consider the same system with a high vacuum reservoir chamber of double the volume of the wound contact chamber. In this case, the quiet period is doubled in comparison to the above example.

Thus, the relationship between quiet periods for an arrangement as shown in FIG. 1, Tcurrent of wound contact chamber volume LW and initial vacuum level VW and an arrangement as shown in FIG. 2 with, in addition to the same elements, a high vacuum chamber of volume $L_{HV}$ and initial vacuum level $V_{HV}$, of quiet period $T_{resv}$ is given by:

$$T_{resv}=T_{current}(V_{HV}/V_W)(L_{HV}/L_W)$$

This relationship is true for wound contact chambers with 100% hysteresis and becomes proportionally larger in effect when lower levels of hysteresis, $H_W\%$, are specified in the wound contact chamber, as given by:

$$T_{resv}=T_{current}(V_{HV}/V_W)(L_{HV}/L_W)(100/H_W\%)$$

Thus, it can be seen that an arrangement as shown in FIG. 2 maintaining a high vacuum reservoir 22 of double the volume of the wound chamber and at double the vacuum level of the wound chamber, for a wound chamber running with 5% hysteresis will have a quiet period approximately eighty-times longer than an equivalent arrangement in line with that shown in FIG. 1, and that this is due to the decoupling of narrow hysteresis from the running of the pump 29 utilising the high vacuum reservoir 22.

The extended quiet period can be of significant duration, depending upon the fluid ingress levels to the system and the above parameters. When the expected fluid ingress level is low, the extended quiet period may be sufficiently long that a system in which the replenishment means can be decoupled from the patient interface can be conceived.

When the user is about to enter a period requiring prolonged system silence, the high vacuum chamber can be fully charged immediately prior to this. By appropriate selection of operating parameters, it is possible for the period of replenishment of the high vacuum reservoir 22 to be sufficiently long to effectively allow the user to specify periods of silent running of several hours immediately following replenishment.

As described above the threshold negative pressure at which the negative pressure in the vacuum reservoir must be replenished may be equal to the desired negative pressure at the wound site. Alternatively, a higher or lower negative pressure may be selected for the threshold negative pressure.

Thus, the prolonged application of a desired negative pressure is enabled at the wound site 21. The reservoir valve connecting the vacuum reservoir 22 to the wound site 21 is fail safe and will only open when there is a loss of vacuum within the wound chamber. Furthermore the valves are selected so as to close when the pressure at the wound site reaches a desired target specified by the pressure valve manufacturer. Thus by connecting a high vacuum reservoir to a wound site via a pressure regulating valve the period for which the desired negative pressure can be maintained at the wound site without operation of the pump 29 can be extended.

An example of a vacuum pressure regulation valve of a type suitable according to certain embodiments of the present invention is the VRD-ANB-CD vacuum regulator as supplied by Beswick Engineering™. It will be appreciated that other fluid flow control valves used to turn on and off a flow of fluid can be utilised according to certain embodiments of the present invention.

The top-up valve 26 may be of a similar type to the reservoir valve 24. Alternatively, the top-up valve may be implemented as a one-way check valve, or as a controllable valve under the control of the control unit 25.

While example negative pressure values have been outlined above, it is envisaged that the negative pressure range applied at the wound site for the apparatus embodying the present invention may be between about −20 mmHg and −200 mmHg (note that these pressures are relative to normal ambient atmospheric pressure thus, −200 mmHg would be around 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg. Aptly the pressure of the wound chamber is between −125 mmHg and −20 mmHg. It will thus be appreciated that negative pressure is taken to mean a pressure that is less than ambient atmospheric pressure.

It will be appreciated that the various tubes are connected to the fluid reservoir via a fluid tight connection which might be either a tight friction fit or a fitting which requires some securing mechanism such as a jubilee clip or the like. Further examples of possible methods of connection may be adhesive, welding or use of a snap together connector for example as manufactured by Colder Products.

The volume of the vacuum reservoir 22 is aptly greater than that of the wound chamber when the system is operational. More aptly, the volume of the vacuum reservoir is more than two-times greater than that of the wound chamber when the system is operational. Even more aptly, the volume of the vacuum reservoir is more than four-times greater than that of the wound interface chamber when the system is operational.

The vacuum reservoir 22 aptly does not exceed the volume of the wound chamber by more than fifty-fold when the system is operational. More aptly, the vacuum reservoir preferably does not exceed the volume of the wound chamber by more than twenty-fold when the system is operational. Even more aptly, the vacuum reservoir does not exceed the volume of the wound chamber by more than ten-fold when the system is operational.

If a separate fluid collection canister is present, the volume of the vacuum reservoir is aptly greater than that of the wound chamber and fluid collection canister combined when the system is operational. More aptly, the volume of the vacuum reservoir is more than two-times greater than that of the wound chamber and fluid collection canister combined when the system is operational. Even more aptly, the volume of the vacuum reservoir is more than four-times greater than that of the wound chamber and fluid collection canister combined when the system is operational.

Furthermore, in this specific embodiment, the vacuum reservoir aptly does not exceed the volume of the wound chamber and fluid collection canister combined by more than fifty-fold when the system is operational. More aptly, the vacuum reservoir does not exceed the volume of the wound chamber and fluid collection canister combined by more than twenty-fold when the system is operational. Even more aptly, the vacuum reservoir does not exceed the volume of the wound chamber and fluid collection canister combined by more than ten-fold when the system is operational.

The vacuum reservoir 22 may be of rigid or flexible design, and if it is the latter may contain filler of low space filling volume to maintain the vacuum cavity. Alternatively, a flexible vacuum reservoir may be unfilled and be allowed to collapse completely in its initial state. In this case, the mechanical properties of the reservoir must be such that it can generate the specified high vacuum when it recovers shape. Such a system may optionally be augmented by an internal element capable of storing mechanical energy, for example a spring of any design.

An alternative vacuum pressure regulator valve for use according to certain embodiments of the present invention is illustrated in FIGS. 11 to 18. The valve element 42 includes a channel element 48 that is formed from first and second resilient sidewall elements 410a, 410b. An inlet element 412 is inserted into a first end of the channel element 48 and holds the first and second sidewall elements 410a, 410b in an open spaced apart position at the first end of the channel element. An outlet element 414 is inserted into a second end of the channel element 48, holding the sidewall elements in an open spaced apart position at the second end of the channel element. The inlet and outlet elements have an open cross-section, and once inserted into the channel element 48 are sealed in place.

The resilient sidewall elements 410a, 410b are able to move between an open configuration, in which a fluid communication path is provided between the sidewall elements to connect the inlet 412 to the outlet 414, and a closed configuration in which inner surfaces of the sidewall elements are in contact, forming a seal that isolates the inlet 412 from the outlet 414.

Aptly, the first and second sidewall elements 410a, 410b are formed from a material that is able to reversibly self-seal when it comes into contact with itself.

In use, the valve element 42 is coupled between two chambers, each chamber containing a negative pressure (i.e. the pressure within the chambers is less than ambient atmospheric pressure). The valve element 42 operates according to pressure differentials across the sidewall elements 410a, 410b, that is between a pressure acting on the exterior of the sidewall elements and negative pressures acting at the inlet 412 and the outlet 414. In the described example, the pressure acting on the exterior of the sidewall elements is ambient atmospheric pressure, although other pressures could be applied.

The sidewall elements 410a, 410b are resilient, and flex in response to the pressure differential across them. Thus, when a negative pressure is applied to at least one of the inlet 412 and the outlet 414, the pressure differential between the atmospheric pressure acting on the exterior of the sidewall element and the negative pressure inside the channel element 48 results in the sidewall elements being pushed together. If the pressure differential across the sidewall elements is of sufficient magnitude, the sidewall elements will be urged together until they come into contact isolating the inlet element 412 from the outlet element 414.

When the sidewall elements 410a, 410b are in the closed configuration, the region in which the sidewall elements abut forms a zero dead-volume tube.

With the sidewall elements in the closed configuration, if the pressure inside the channel element 48 approaches ambient atmospheric pressure, the pressure differential at the sidewall elements is reduced and the resilient sidewall elements will relax into the open configuration, providing a fluid communication channel between the inlet element 412 and the outlet element 414.

The pressure differential that must be applied to the valve element 42 to cause the sidewall elements 410a, 410b to move to the closed configuration is determined by the device geometry, the construction materials used, and the fluid enclosed within the channel element 48.

Figure 5:
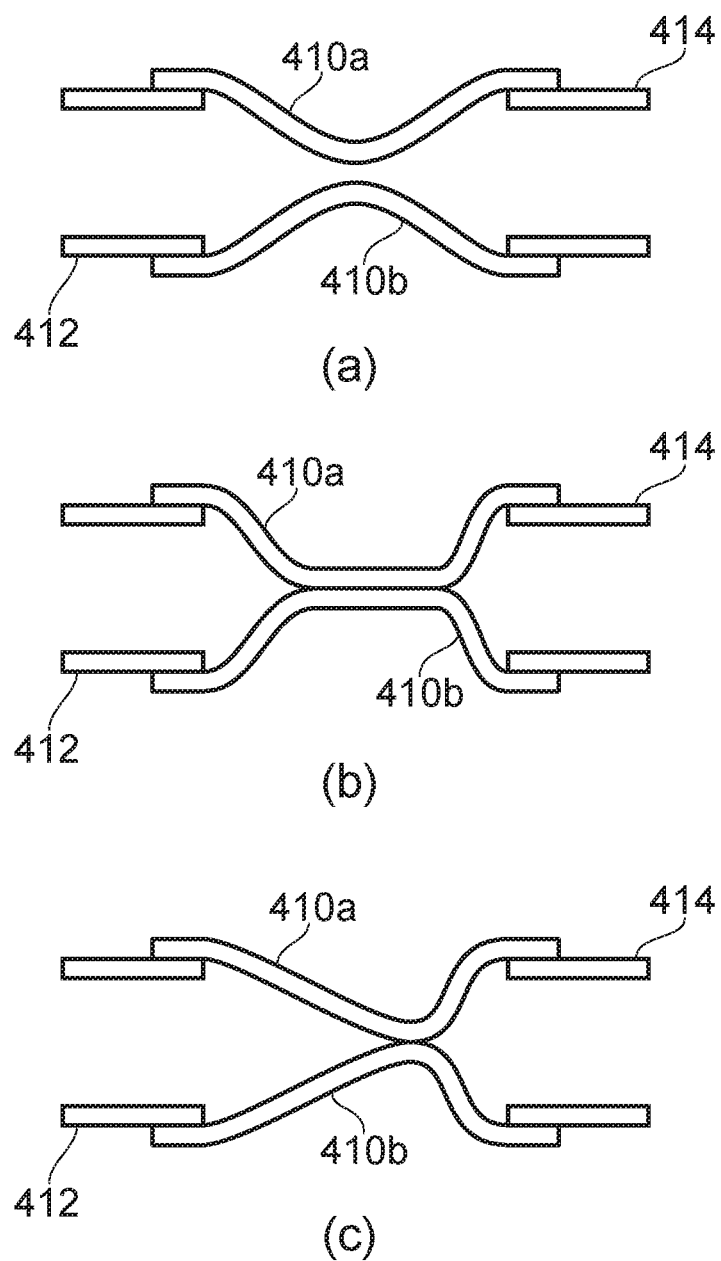
FIG. 5 illustrates cross-sections through a valve element during operation.

FIG. 5 shows cross-sections of the valve element 42 in a number of operational states. In FIG. 5(a), the valve element is coupled between two chambers each containing a pressure close to ambient atmospheric pressure. No significant pressure differential is present across the sidewall elements 410a, 410b, and therefore the valve element 42 is in its initial open configuration. In this configuration the inlet and outlet elements effectively hold the sidewalls apart. As the channel element 48 is open, a fluid communication path is present through the channel connecting the inlet 412 to the outlet 414.

FIG. 5(b) shows a cross-section of the valve element 42 when the valve element is coupled between two chambers containing negative pressures of sufficient magnitude to close the valve, as might be encountered if a source of negative pressure was coupled to the chamber connected to the outlet of the valve element 42 and the system was evacuated. For the valve element of FIG. 5(b), the pressure at the outlet 414 is lower in absolute terms than that at the inlet 412.

In this case, the pressure differential across the sidewall elements 410a, 410b acts to push the sidewall elements together until the inner surfaces of the sidewall elements come into contact in a central region of the channel element 48. A temporary seal is formed in the contact region where the sidewall elements 410a, 410b abut, isolating the inlet 412 from the outlet 414. This allows a higher level of negative pressure (i.e. a lower absolute pressure) to be present at the outlet element 414 than at the inlet element 412.

If fluid leaks either intentionally or unintentionally into the chamber connected to the inlet element 412, the negative pressure at the inlet element will degrade and start to approach ambient atmospheric pressure. As the pressure at the inlet element degrades, the pressure differential across the sidewall elements 410a, 410b in a region near the inlet element will decrease. This leads to the sidewall elements 410a, 410b starting to peel apart from the first end of the channel element 48. If the negative pressure at the inlet 412 degrades to a threshold level, the sidewall elements 410a,

410b will peel apart until the seal between them is broken and the fluid communication path between the inlet and the outlet is restored.

FIG. 5(*c*) shows a cross-section of the valve element 42 at the point where the sidewall elements have peeled apart from the first end of the channel element 48 in response to the negative pressure at the inlet element degrading to the threshold level. As the sidewall elements 410*a*, 410*b* move into the open configuration, the fluid communication path allows negative pressure to be communicated from the outlet 414 to the inlet 412, replenishing the negative pressure in the chamber connected to the inlet element 412 via the greater negative pressure in the chamber connected to the outlet element 414.

As the negative pressure in the chamber coupled to the inlet element 412 is replenished, the pressure differential across the sidewall elements 410*a*, 410*b* near the first end of the channel element 48 will increase urging the sidewall elements together and throttling the communication of negative pressure between the inlet and outlet elements.

The threshold pressure at the inlet element 412, at which the valve opens and closes can be controlled by selection of the device geometry, construction materials and the enclosed fluid within the valve element 42.

Figure 6:
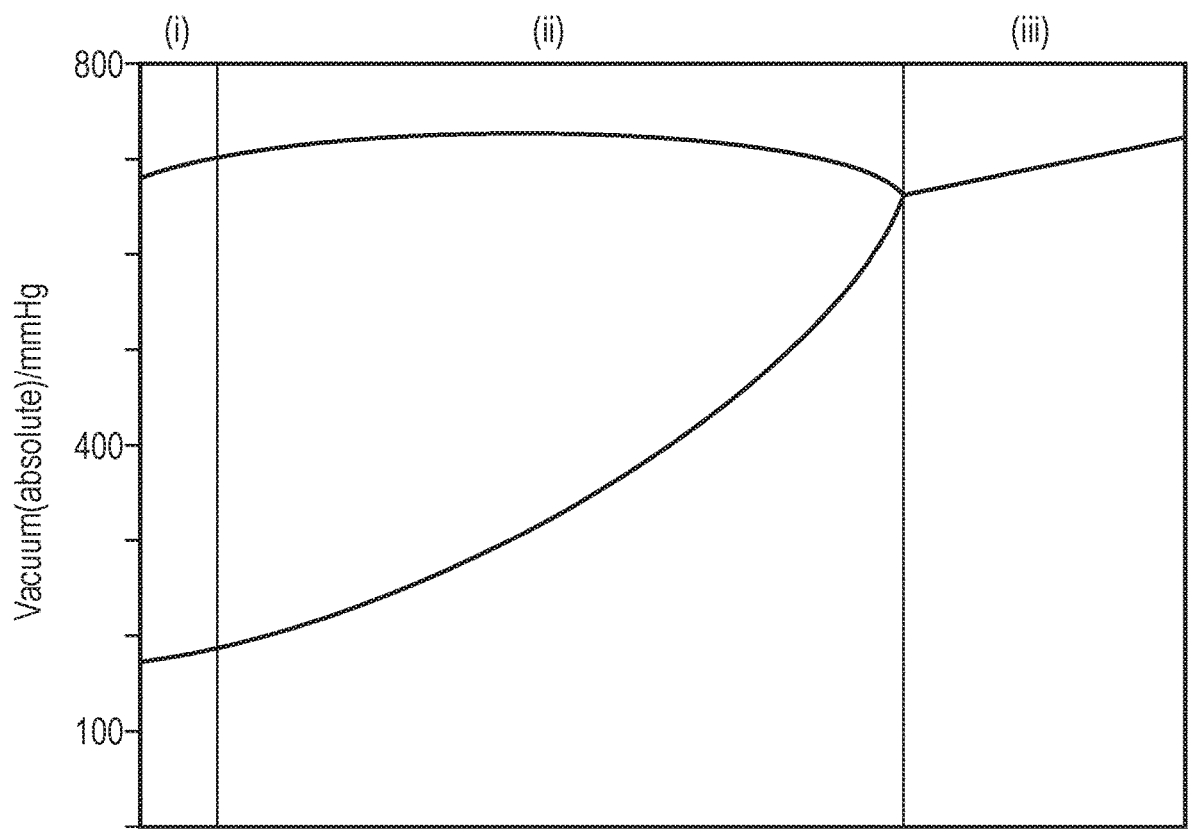
FIG. 6 illustrates a graph of operating pressures in two chambers connected via a valve element.

FIG. 6 shows a graph illustrating pressure against time for an example scenario in which two chambers, each of 50 ml in volume, are coupled via the valve element 2. Initially, a first chamber coupled to the inlet element 12 was evacuated to a negative pressure of approximately −65 mmHg (i.e. 700 mmHg absolute), and a second chamber coupled to the outlet element 14 was evacuated to a negative pressure of approximately −585 mmHg (i.e. 180 mmHg absolute). A leak of 50 ml/h was introduced into the first chamber, and the negative pressure level in both chambers was recorded for approximately an hour. Initially, the valve element will be in a configuration similar to that shown in FIG. 5(*b*).

In an initial stage (i) the pressure in the first chamber is seen to steadily decrease, and the pressure in the second chamber is maintained at a constant level. As the negative pressure in the first chamber decreases, the pressure differential across the sidewall elements at the first end of the channel element decreases and the sidewall elements begin to peel apart. When the negative pressure in the first chamber reaches the threshold value, the valve element 42 begins to open as can be seen in stage (ii).

In stage (ii), the negative pressure level in the second chamber can be seen to decrease, as negative pressure is communicated from the second chamber to the first chamber to compensate for the leak. The level of negative pressure in the first chamber can be seen to degrade at a slower rate as the valve element 42 opens, and then steadily the negative pressure in the first chamber is replenished.

Eventually, the negative pressure in the second chamber degrades to the level of the negative pressure in the first chamber, as can be seen in stage (iii). At this point, the valve element 42 is fully open and the negative pressure in the first and second chambers is equalized. The negative pressure in both chambers then continues to degrade at the leak rate.

The valve element 42 can be used in any application requiring a specified level of vacuum to be transmitted to and or maintained in a system. For example, some medical applications require the application of negative pressure to a bodily location. The level of vacuum supplied by a vacuum pump (in situ or via a wall-line) may be excessive for the chosen application. By coupling the valve element 42 between the vacuum source and the site of application, the level of negative pressure applied can be regulated to not exceed the level specified by the threshold negative pressure of the valve element 42. One example medical application is the provision of negative pressure at a wound site in topical negative pressure therapy.

Figure 10:
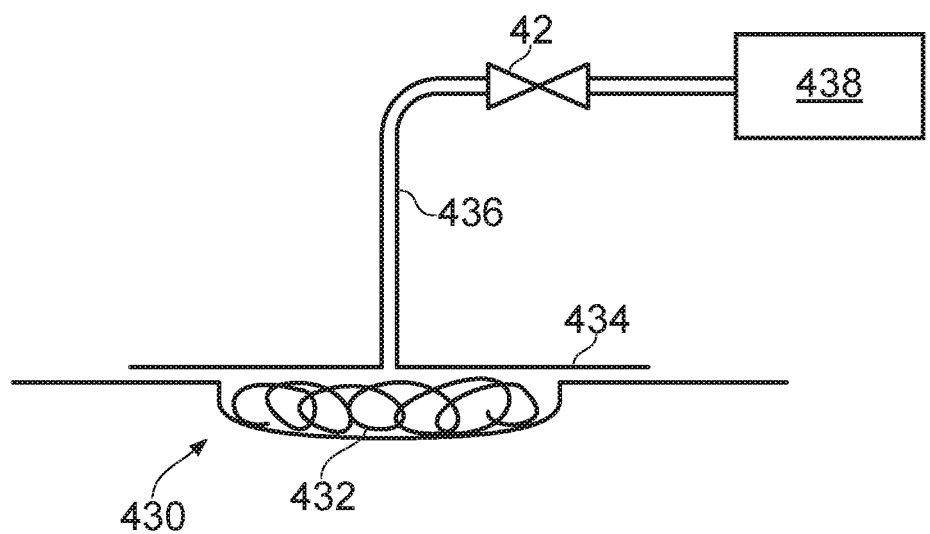
FIG. 10 illustrates an arrangement for applying negative pressure to a wound site including a valve element.

FIG. 10 shows an example arrangement including the valve element 42 for applying topical negative pressure to a wound site 430. A packing material 432, such as foam, gauze or the like, is placed within a wound cavity, and then a drape 434 is sealed to the surface of the skin around the wound site 430 forming a fluid tight seal around the perimeter of a wound chamber. A source of negative pressure 438, such as a negative pressure reservoir, is coupled to the wound cavity via the valve element 42 and a tube 436. Optionally, a fluid collection canister (not shown) may be coupled between the valve 42 and the wound chamber to collect any wound exudate drawn from the wound site 430. The use of the packing material 432 is optional, and it may be omitted in certain arrangements as appropriate.

The negative pressure reservoir 438 may be connectable to a powered source of negative pressure operable to evacuate the system down to initial negative pressure levels.

Whilst embodiments of the present invention will be described hereinafter by way of reference to a wound chamber defined at a wound site under a drape it will be understood that certain embodiments of the present invention can be utilised to maintain a negative pressure in a wound chamber which is a rigid structure or partly rigid structure such as a cup device placed over a wound site.

Initially, the wound site and the negative pressure reservoir 38 are at ambient atmospheric pressure. A powered source of negative pressure is then coupled to the negative pressure reservoir 438 and operates to evacuate the system. As the pressure at the inlet and outlet elements is initially at ambient atmospheric pressure, the valve element 42 will be in its initial open state, as shown in FIG. 5(*a*). Thus, negative pressure generated in the negative pressure reservoir 438 will be communicated through the open valve element 42 to the wound site 430.

Once the negative pressure at the wound site, and therefore at the inlet element 412, reaches a threshold level the pressure differential acting on the sidewall elements 410*a*, 410*b* will urge the sidewall elements together, closing the valve element 42, as shown in FIG. 5(*b*). The powered source of negative pressure can then continue to evacuate the negative pressure reservoir, isolated from the wound site 430 by the valve element 42. Thus, the negative pressure established in the negative pressure reservoir 438 may be higher, that is more negative, than that experienced at the wound site 430. Once the desired level of negative pressure is established in the negative pressure reservoir 438, the powered source of negative pressure can be disabled or removed from the system.

Over time, small leakage paths will form that allow fluid to leak into the wound chamber. Ingress of fluid such as wound exudate or gas into the wound chamber will lead to the negative pressure at the wound site slowly degrading, i.e. the pressure becoming less negative. Once the negative pressure at the wound site 430 degrades to a certain level, the valve element 42 will begin to open, as shown in FIG. 5(*c*), allowing negative pressure to be communicated from the negative pressure reservoir 438 to the wound site 430 to replenish the negative pressure at the wound site. The negative pressures at the wound site and in the negative pressure reservoir will follow a profile similar to that shown in FIG. 6.

Thus, the valve element 42 is able to automatically control the communication of negative pressure from the negative pressure reservoir 438 to the wound site 430 in order to maintain the negative pressure applied to the wound site within certain limits. Once the negative pressure in the negative pressure reservoir 438 equalizes with the negative pressure at the wound site, the powered source of negative pressure may be used to re-establish the initial level of negative pressure in the negative pressure reservoir.

The volume of the vacuum reservoir 438 is preferably greater than that of the wound chamber when the system is operational. This extends the time period for which the negative pressure reservoir 438 is able to maintain the negative pressure at the wound site 430 within the desired limits.

Alternatively, the negative pressure reservoir 438 may be omitted and the valve element 42 may be coupled between the wound site 430 and a powered source of negative pressure such as a pump, or an external vacuum line. The negative pressure provided by the pump or the vacuum line may be too great in value to be applied directly to the wound site. However, by coupling the valve element 42 between the source of negative pressure and the wound site, the negative pressure applied at the wound site 430 will be regulated according to the threshold negative pressure value of the valve element 42.

It is envisaged that the negative pressure range applied at the wound site for the apparatus embodying the present invention may be between about −20 mmHg and −200 mmHg (note that these pressures are relative to normal ambient atmospheric pressure thus, −200 mmHg would be around 560 mmHg in practical terms). Aptly, the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg. Aptly the pressure of the wound chamber is between −125 mmHg and −20 mmHg. It will thus be appreciated that negative pressure is taken to mean a pressure that is less than ambient atmospheric pressure.

It will be appreciated that the various tubes are connected via a fluid tight connection which might be either a tight friction fit or a fitting which requires some securing mechanism such as a jubilee clip or the like. Further examples of possible methods of connection may be adhesive, welding or use of a snap together connector for example as manufactured by Colder Products.

Figure 7:
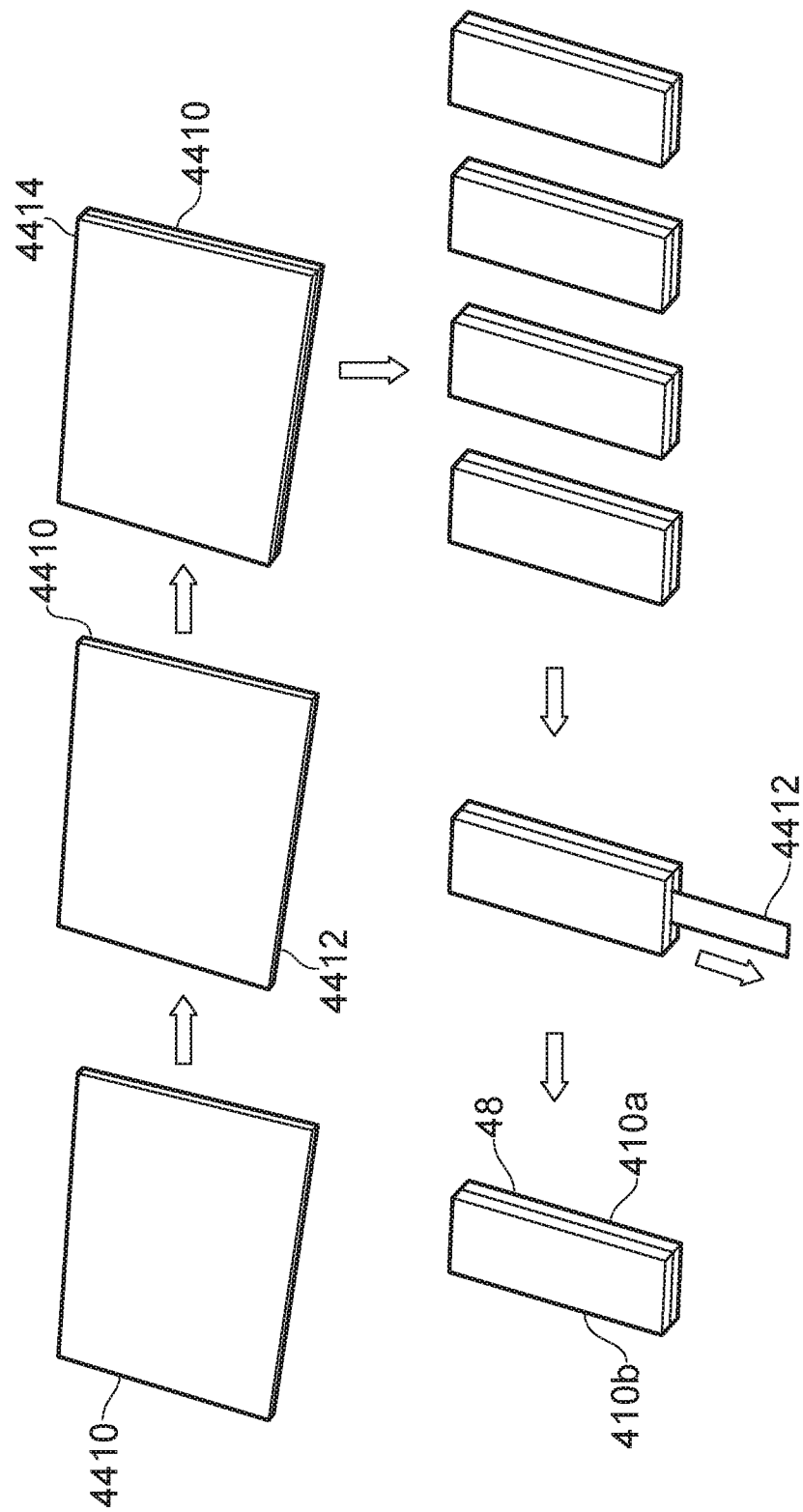
FIG. 7 illustrates a method of manufacturing a channel element.

FIG. 7 illustrates an exemplary method of fabricating the channel element 8 for manufacturing the valve element 2. According to the illustrated method, in a first step of the method a first flat sheet 410 of elastomeric material is cast, for example a 2 mm thick sheet of 300 mm by 300 mm formed of a two-part heat-curable silicone elastomer (for example Wacker Chemie AG), or a polyurethane elastomer. Masking strips 412, for example strips of acetate sheet having a width of 10 mm and a thickness of 50 µm, are laid upon the first flat sheet 410 allowing sufficient spacing to separate individual channel elements when complete. A second flat sheet 414 of elastomeric material is then cured in situ on top of the first sheet 410, sandwiching the acetate strips in place. The individual flat tubes, forming the channel elements, are then separated from each other and cut to a desired length (for example 40 mm). The acetate strips 412 can then be removed from each of the flat tubes, resulting in reversibly self-sealing channel elements 8 comprising tubes of zero dead-volume.

It will be understood that the term dead-volume relates to the volume enclosed within the channel element 48 when the tube is in its initial closed position. In the above described channel elements 48, the sidewall elements abut along the length of the channel once the acetate strips 4412 have been removed. Thus, there is no volume enclosed between the sidewall elements 48, resulting in a zero dead-volume tube. In contrast, attempting to flatten a tube of cylindrical cross-section would inevitably lead to pinched regions at the edges of the flattened tube having some dead-volume through which fluid could continue to flow.

Figure 8:
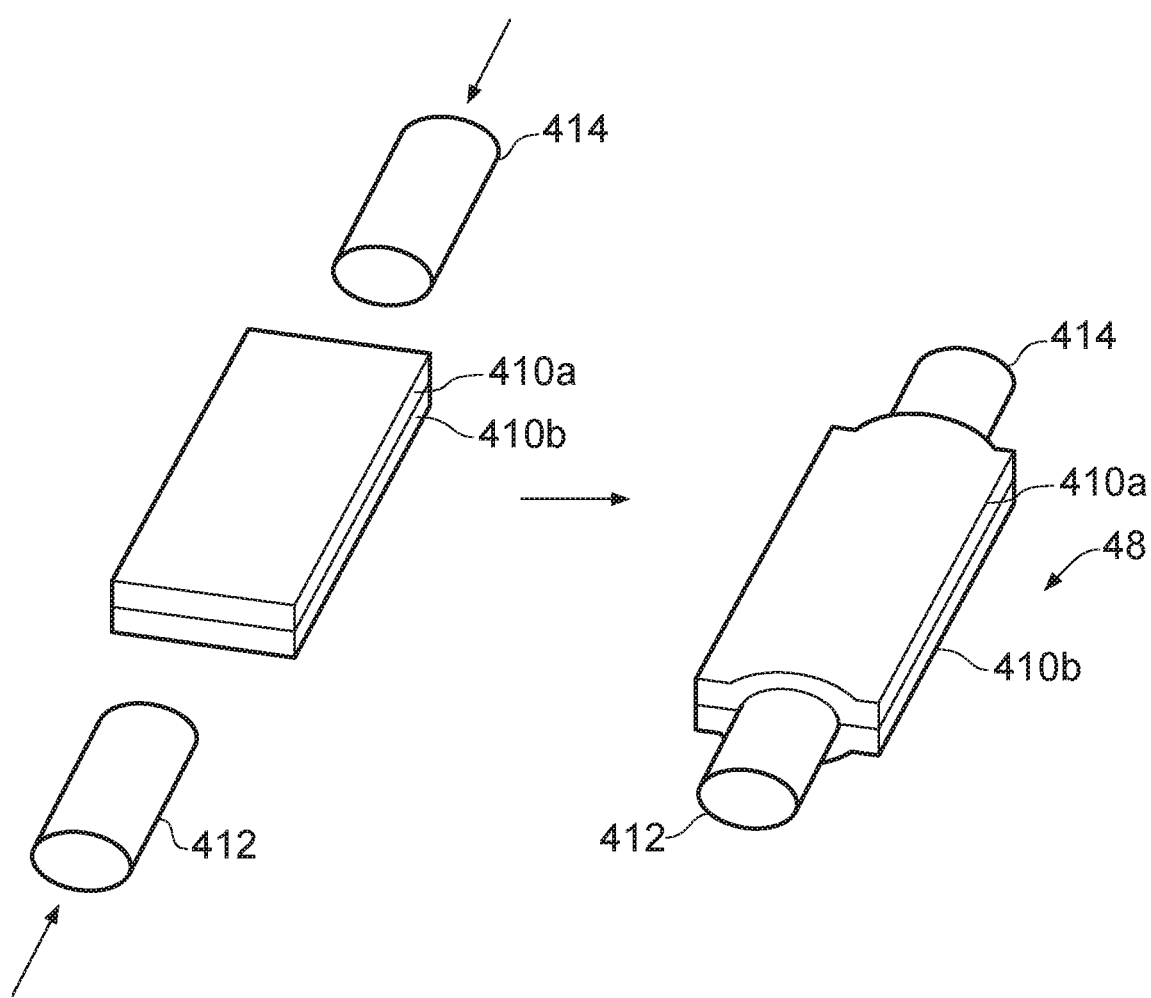
FIG. 8 illustrates assembly of a valve element.

In order to form the valve element 42, the inlet element 412 and outlet element 414 are inserted into opposite ends of the channel element 48, as illustrated in FIG. 8. The inlet and outlet elements are of open cross-section, for example tubing of open aspect having an internal diameter of 4 mm and an external diameter of 8 mm. The inlet and outlet elements hold apart the sidewall elements 410a, 410b of the channel element 48 at the respective ends of the channel element.

The threshold operating pressure of the valve element 42 can be configured by setting the end-to-end separation of the inlet and outlet elements, that is the distance between the ends of the inlet and outlet elements inserted into the channel. The end-to-end separation required to configure a certain threshold operating pressure depends on the materials used in the construction of the valve element, and the dimensions of the channel element. In the example illustrated in FIG. 6, an end-to-end separation of 10 mm was used.

Figure 9:
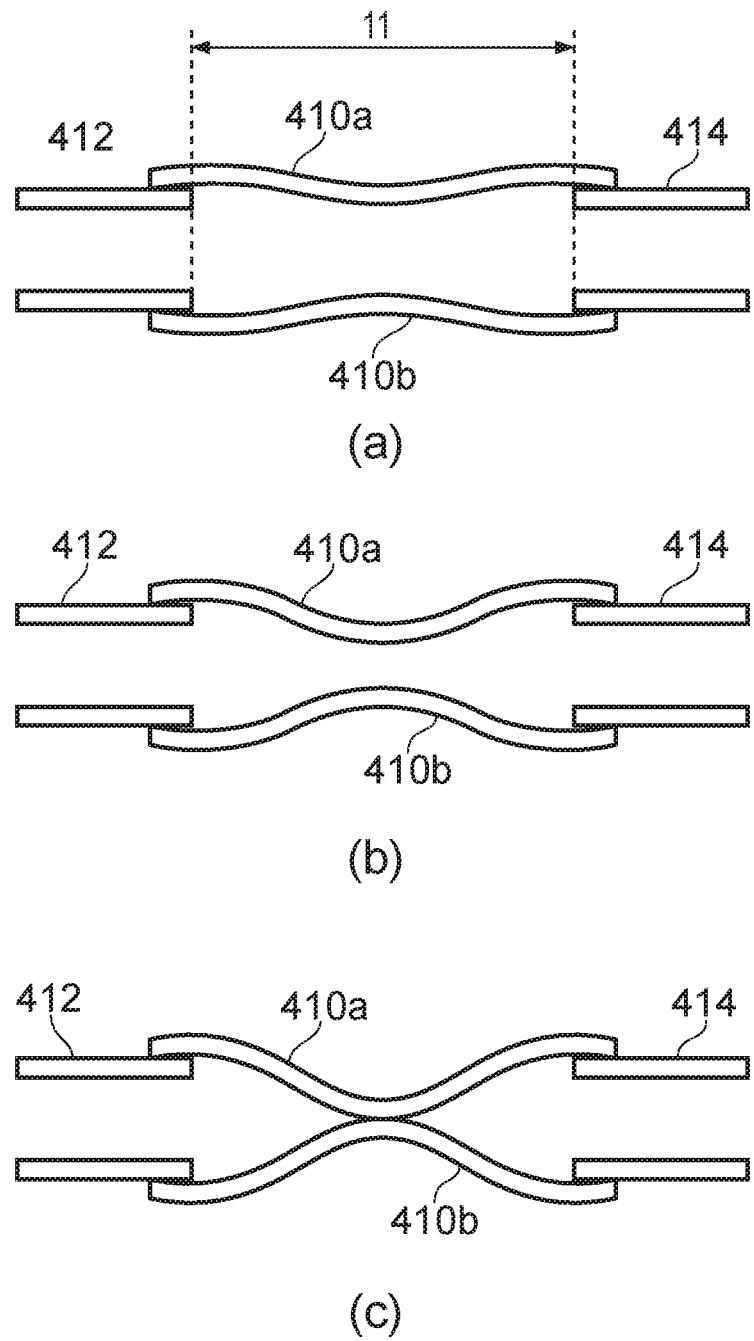
FIG. 9 illustrates cross-sections through a valve element having different mounting spacings.

FIG. 9 shows cross-sections of valve elements with no pressure differential applied to the sidewalls and having different end-to-end separations 411 of the inlet and outlet elements 412, 414. For the valve element illustrated in FIG. 9(*a*), the end-to-end separation 411 is too short, meaning that the valve will not close as desired or will have a very high threshold negative pressure (i.e. very low absolute threshold pressure). Conversely, if the end-to-end separation 411 is too large as shown in FIG. 9(*c*), the valve element may be initially closed when no pressure differential is applied. The valve element 42 shown in FIG. 9(*c*) will therefore be unable to regulate a negative pressure; however such a valve element may be operable to selectively provide a fluid communication path if a positive pressure (greater than ambient atmospheric pressure) is applied to the inlet and outlet elements.

FIG. 9(*b*) illustrates a cross-section of a valve element 42 having an end-to-end separation 411 of the inlet and outlet elements such that the valve element will be operable to regulate the communication of negative pressure.

For a valve element fabricated according to the method described in relation to FIGS. 7 and 8, it has been found that a valve element with an end-to-end separation 11 of 3 mm did not shut (DNS) when an absolute pressure of 180 mmHg was established at both the inlet and the outlet. Conversely, a valve element having an end-to-end separation of 15 mm or more was permanently closed even when no pressure differential was present across the sidewall elements. In between these extremes, it was found that the threshold operating pressure (absolute) of the valve element increases with increasing end-to-end separation, and therefore the negative pressure level required for closure decreases with increasing end-to-end separation 411.

Table 1 shows experimental results for the pressure at the inlet 412 at closure for valve elements fabricated according to the above described method having end-to-end separations 11 of 3 mm, 7 mm, 10 mm, and 12 mm. The valve elements where coupled between two chambers at ambient atmospheric pressure, and then the system was evacuated down to 180 mmHg absolute pressure via a pump connected to the chamber coupled to the outlet 414. The pressure at which the valve element closed was recorded. This procedure was repeated ten times for each valve element, and the results are recorded in Table 1. Pressures values in Table 1 are absolute pressures in units of mmHg.

TABLE 1

| 3 mm | 7 mm | 10 mm | 12 mm |
|---|---|---|---|
| DNS | 507 | 715 | 716 |
| DNS | 525 | 722 | 732 |
| DNS | 519 | 721 | 732 |
| DNS | 519 | 719 | 732 |
| DNS | 513 | 722 | 734 |
| DNS | 516 | 720 | 734 |
| DNS | 514 | 717 | 730 |
| DNS | 517 | 718 | 735 |
| DNS | 513 | 716 | 731 |
| DNS | 524 | 719 | 732 |

As can be seen from Table 1, the threshold pressure for the valve element 42 is strongly dependent on end-to-end separation 411 of the inlet 412 and outlet 414 elements, allowing the valve element to be constructed for a desired threshold pressure by controlling the end-to-end separation.

As will be understood, for a valve element made from different materials, or having different sidewall thicknesses, the end-to-end separation 411 required for a particular threshold pressure will vary from the examples given above.

As the channel element 48 is constructed as a zero dead-volume tube, the region in which the sidewall elements 410*a*, 410*b* abut when in the closed configuration will form a zero dead-volume seal, that is there will be no volume in which fluid may be trapped between the sidewall elements within the region of the channel element where the sidewall elements abut.

Another example of a pressure regulator valve is thermo formable plastic tube which is heat deformed by making contact with a heated element under controlled temperature pressure and time resulting in a tube that collapses with certain internal reduced pressure or vacuum compared to the external pressure.

It would be known to the skilled person that any plastic that could be deformed by a heat treatment could be suitable as the material for the thermo formable plastic tube of the present invention. There may be one or more heating elements to produce the deformed channel or tube. It is possible that one heat element could be used in the heat and pressure process to produce a deformed channel or tube. It is even foreseen that one heat element could be used and the channel or tube or rotated to deform the channel or tube in various places to give the final deformed channel or tube. The heat and pressure process may be repeated, using the same heat and pressure measurements or different temperature, pressure and durations as required to give the final deformed channel or tube. In a preferred heat and pressure process two or more opposing heating elements would be used in a single compressing action on the tube.

Preferably the thermo formable plastic is a thermoplastic elastomer (TPE), thermoplastic elastomers are well known in the art and their properties are well known.

Suitable thermoplastic elastomers (TPE) (thermos formable elastomers) include but are not limited to, all six generic classes of TPEs, which are Styrenic block copolymers, polyolefin blends, elastomeric alloys (TPE-v or TPV), thermoplastic polyurethanes, thermoplastic copolyester and thermoplastic polymides. Examples of TPE products that come from block copolymers group are Amitel (DSM), Engage (Dow chemical), Hytrel (Du Pont), Kraton (Shell chemicals), Pebax (Arkema), Pellethane, Riteflex (Ticona), Styroflex (BASF) and more. While there are now many commercial products of elastomer alloy, these include: Alcryn (Du Pont), Dryflex, Evoprene (AlphaGary), Forprene, Geolast (Monsanta), Mediprene, Santoprene and Sarlink (DSM).

Any suitable width of a heating element for deforming the tube could be used depending on the required properties of the tube, for example the reduced pressure in which cause collapse and closure of the tube.

Typical width of a suitable heating element may be 2 to 15 mm, 3 to 13 mm, 5 to 12 mm or any other suitable width.

The suitable width of the heating element may be dependent on the type of tube and its properties e.g. diameter, wall thickness, material construction.

For a tubing of Outer Diameter (OD) 12 mm a suitable width of heating element may be 2 to 20 mm.

The temperature used to deform the tube can be any suitable temperature to deform the tube and may depend on the properties of the tube diameter, wall thickness, material and construction.

Typically this maybe 80 to 180° Celsius (C.), 80 to 165° C., 90 to 110° C., 93 to 107° C., 95 to 105° C., 97 to 101° C., 98 to 100° C. etc.

The deformation time may also be dependent on the properties of the tube and heat element process and can be any suitable duration required to deform the tube to the desired properties. This could be a matter of a few seconds or more e.g. 3 seconds.

After deformation by heat as explained above, the tube may require a setting or cooling period to maintain the geometry or properties of the deformation.

This again will depend on the starting materials, tube, heat element, pressure, time of deformation etc.

The setting or cooler period could be for example 80° C. for 10 minutes.

It is foreseen that the deformation and setting period could be a function of time and temperature.

Also, the heat deformation process may have the heated elements pinched for the required heating time and then released, with the cooling period taking place without the heating element in contact with the tube.

Or in other embodiments the heating element may remain in contact with the tube during the cooling/setting period.

The cooling/setting period may not be time dependent but depending on reaching a target temperature e.g. from around 100° C. at the heat element process to a final setting/coolant temperature of e.g. 80° C.

The heated deforming element/bar may be any suitable shape or geometry for example flat, curved including semi-circular, and in flat with radius edges.

It is foreseen that in the heat deforming process that there are two heated forming bars in which between these heated deforming bars the plastic tube/TPE tube is placed prior to the heat deforming process.

It is foreseen that the heated bars clamp or compress the plastic/TPE tube deforming the tube.

Figure 12:
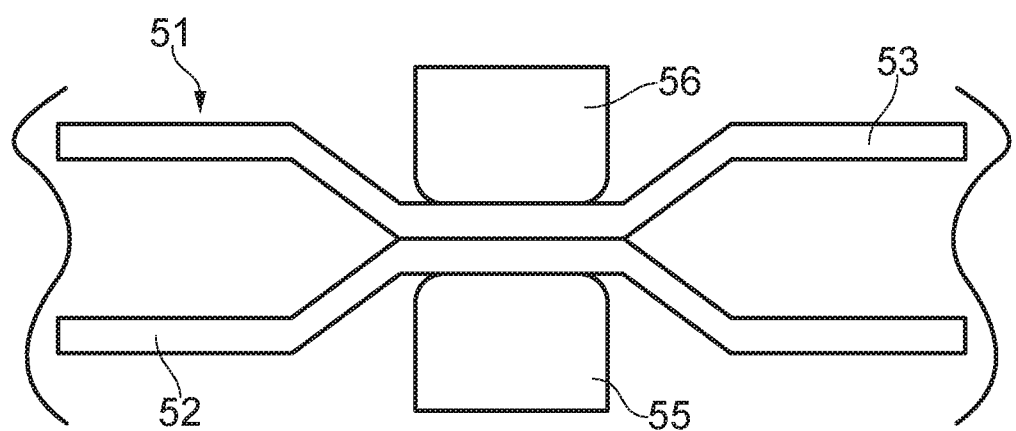
Figure 13:
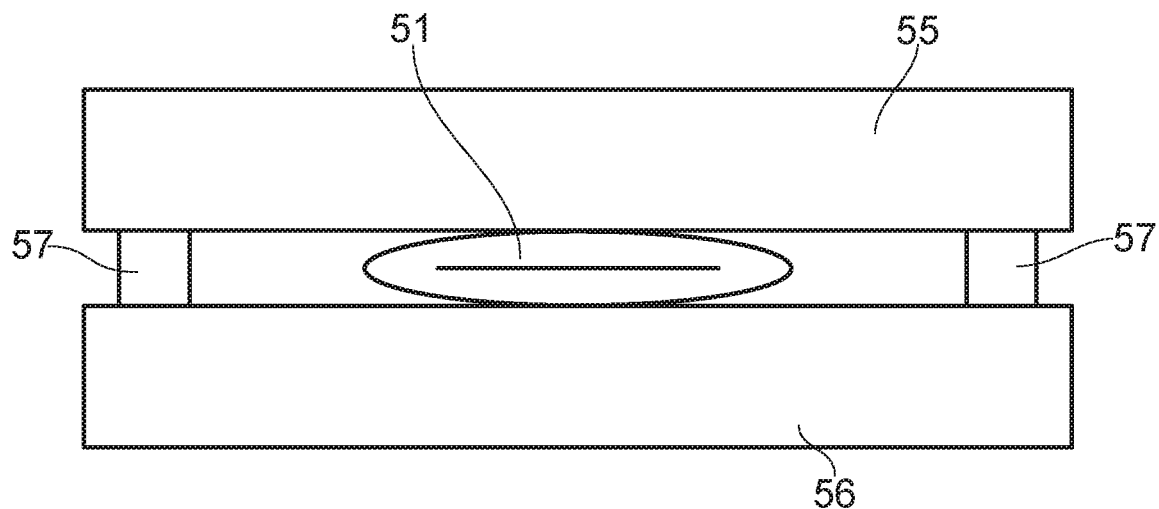
FIG. 13 illustrates an alternative manufacturing process for a deflatable tube valve.

The two bars may fully compress the tube according to an applied pressure (as illustrated in FIG. 12) and or may compress the tube to a desired separation/distance as illustrated in FIG. 13.

Figure 11:
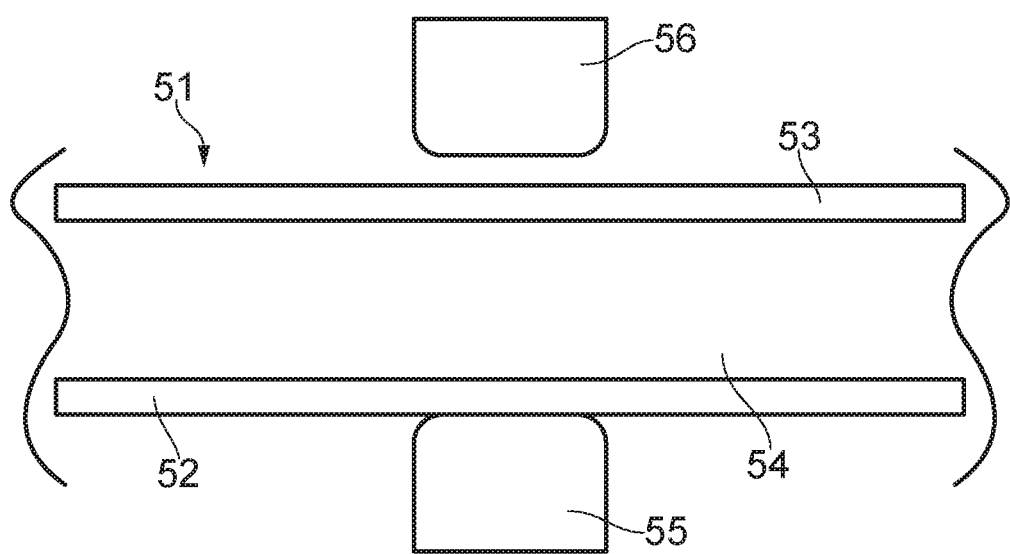

FIG. 11 illustrates a tube or channel element 51 with two opposing side walls 52 and 53, defining a channel 54. The tube is placed in-between two heating elements 55 and 56. FIG. 11 shows the channel open, and before a heat and pressure process.

FIG. 12 illustrates that the heating elements 55 and 56 have pinched the tube 51 creating on the two opposing side walls 52 and 52 a substantial flat portion where the heating elements 55 and 56 compressed the tube 51. FIG. 12 illustrates the heat and compression process.

FIG. 13 illustrates and alternative embodiment of the heat and compression process where the heating elements 55 and 56 are prevented from coming into contact with each other by stops 57 and thus the tube 51 is not completely crushed. The size of the stops 57 may vary according to the size of the tube 51 and the desire compression required in the heat and compression process.

According to the invention there is provided a method of manufacturer of a channel element for selectively providing a fluid communication path, the method comprising:

subjecting a channel element to a deformation process in which the opposing sidewalls of the channel element are deformed to aid movement between an open configuration when the opposing side walls are apart and a closed configuration when the opposing side walls abut, to close or open the channel of the channel element, responsive to a pressure difference at or on the side walls between the inside surface and the outside surface of the opposing walls.

According to the invention there is provided a channel element for selectively providing a fluid communication path, comprising:

a deformed channel in which the opposing sidewalls of the channel element are deformed to aid movement between an open configuration when the opposing side walls are apart and a closed configuration when the opposing side walls abut, to close or open the channel of the channel element, responsive to a pressure difference at or on the side walls between the inside surface and the outside surface of the opposing walls.

The channel element may be a tube. This tube may be circular, oval, square, rectangle, elliptical or any other suitable shape. The tube may be cross sectioned. The channel element may be irreversibly deformed by the process. The channel element or tube mat be deformed by a heat and pressure process that deforms the channel element or tube whether this is irreversibly deformed or not.

The valves according to the present invention can be used in many situations. The valves may be used with further integral tubing or channels, or be used where further tubing or channels are attached at one or more ends of the valve to allow fluid communication between two points. In the cases where integral tubing is inserted into the ends, this tubing may be optionally be used to hold the side wall elements apart in a manner similar to the previous flat valve embodiment described herein.

It is foreseen that the present invention could be used in a negative pressure treatment system similar to but not limited to that described in FIG. 2, with a wound dressing, pump to create the negative pressure, possibly a canister to collect the wound exudate although in alternative systems, the dressing is able to do this function without the need for a canister for example by employing a superabsorber material in the dressing.

The dressing could be various dressings known in the art and used for such purposes. Typically the dressing will have a cover and wound spacer material or a material to collect the exudate. The negative pressure treatment system would usually have various tubes and valves allowing fluid communication between the various components in order for the system to work. For example a channel or tube from the wound area to the canister and then to the pump.

The dressing may have a seal to aid sealing of the dressing to the skin of the patient. The sealant may be any known in the art and could include but not limited to silicon adhesives and or acrylics. Specific examples could include but again not be limited to are Duoderm from ConvTec and Replicare from Coloplast.

EXAMPLE 1

Preparation of a Vacuum Valve by Partially Sealing Continuous Tubing

Figure 14:
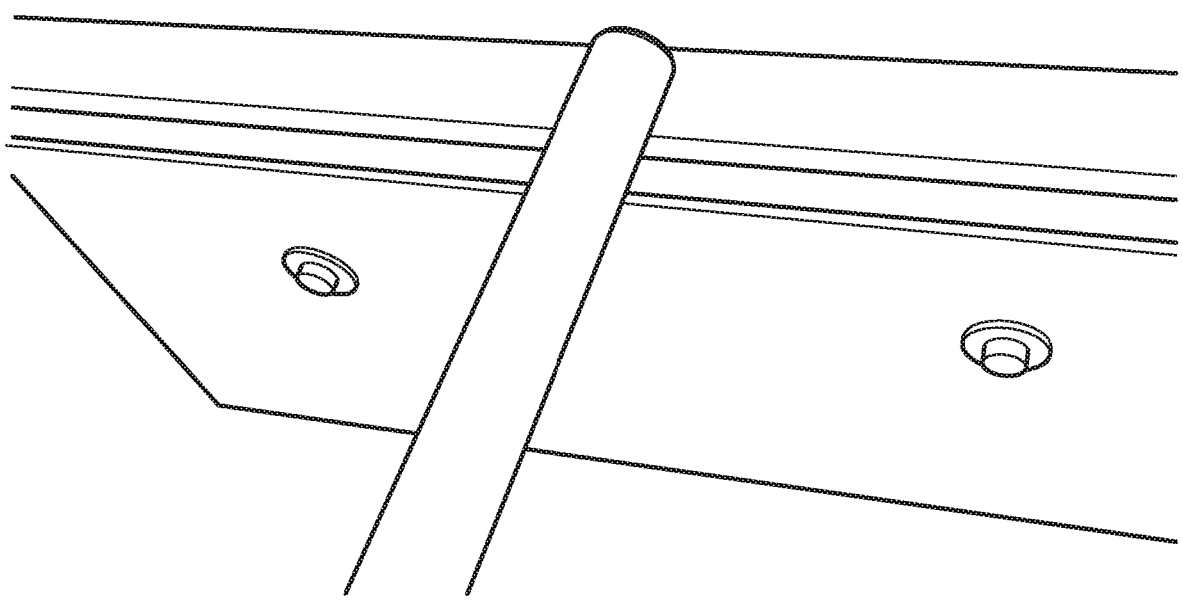
FIGS. 14, 15, 16, 17 and 18 illustrate the manufacture of a specific embodiment of the deformed tube valve.
Figure 15:
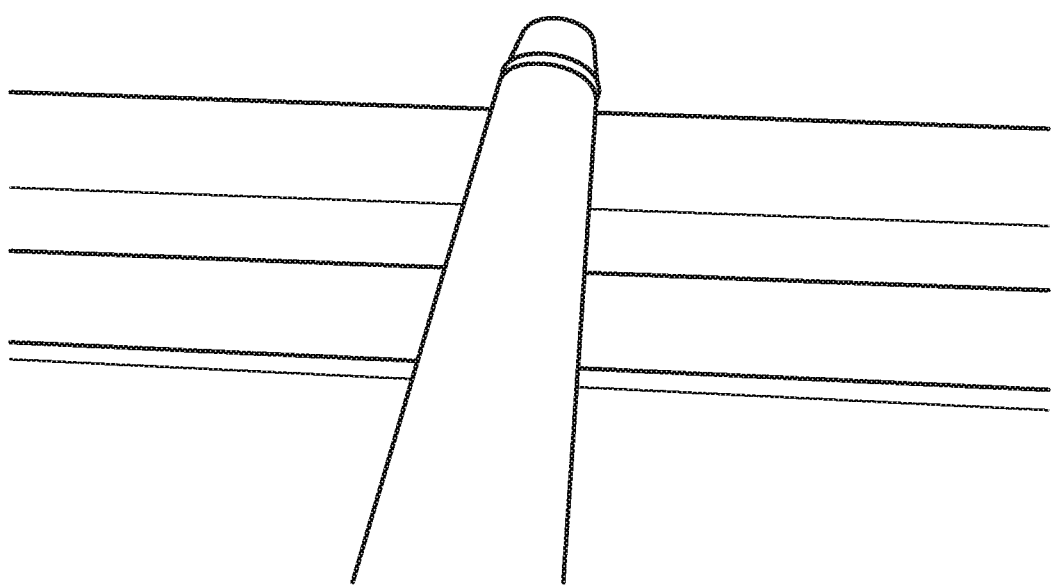

Thermoplastic elastomeric (TPE) tubing (Cole-Parmer, Clear C-Flex tubing, item WZ-06422-15) of ½" OD (12 mm) and ⅜" (9 mm) ID, as illustrated in FIG. 14 was heat sealed with a 9 mm wide heating element in a direction perpendicular to its long axis, as illustrated in FIG. 15 at a temperature of 98-100° C. for a welding time of 3.0 seconds, at 3 Bars pressure (300 kilo-Pascals) and cooled to 80° C. prior to sealer jaws releasing the sample.

Figure 16:
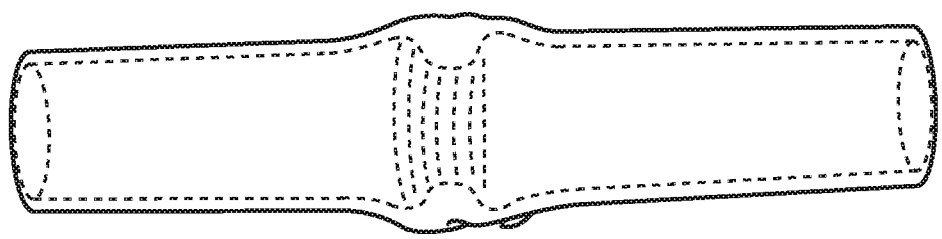
Figure 17:
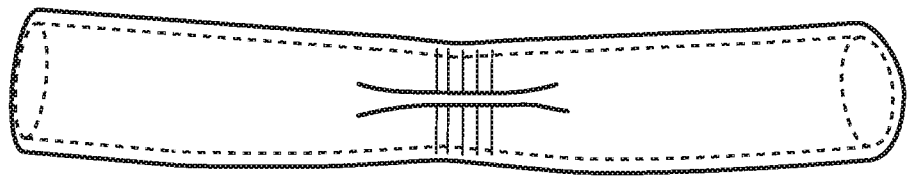
Figure 18:
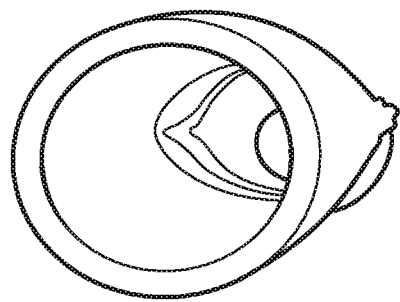

The result was a partially deformed tube, deformed at the sides of the tube (the area receiving maximum pressure) but remaining unsealed across its centre, as illustrated in FIGS. 16, 17 and 18.

The tubing was trimmed in a direction perpendicular to the long axis of the tube at a distance of 40 mm from the weld.

EXAMPLE 2

Performance of a Vacuum Valve by Partially Sealing Continuous Tubing

The valve prepared in Example 1 was fitted to a source of vacuum and vacuum gauges were placed between the source of vacuum and the valve and on the side of the valve distal to the vacuum source. The vacuum source was turned on and generated a vacuum of 202 mmHg on the proximal side of the valve while the vacuum was 557 mmHg on the distal side of the valve, thus demonstrating the operation of the valve. The ambient pressure was 756 mmHg, thus the valve closed at a vacuum of 200 mmHg below ambient atmospheric pressure.

EXAMPLE 3

Of a Vacuum Regulation Valve Prepared by Heat-Sealing a Thermoplastic Elastomeric Tube Transparent thermoplastic elastomer tubing (Clear C-flex tubing, ⅜" ID (9 mm), ½" (12 mm) OD, Cole-Parmer Instrument Company Ltd) was cut to a 100 mm length and heat-sealed in a direction perpendicular to its longest axis at its mid-point. The heat sealer used was a Hulme Martin HM1000P Portable heat sealer with a 3 mm band run on heat setting 10 and cooling setting 10, 315 W per seal. Only one of the jaws of this heat sealer is heated and so the tube was rotated along its long axis by half a turn and the procedure repeated. This process was repeated 3-times in each orientation. Following this, the same process was repeated, 2-times in each orientation, on both adjacent sides of the central 3 mm wide band, resulting in a heat-sealed section approximately 10 mm in width. This process did not seal the tube but generated crimped internal folds that enabled the tube to fully seal across its width when containing a vacuum.

The valve described above had a closing pressure of 200 mmHg below ambient atmospheric pressure.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A vacuum pressure regulator valve produced by a process comprising:
    compressing first and second opposing sidewalls of a first portion of a tube toward one another in a direction transverse to a longitudinal axis of the tube to move the first and second opposing sidewalls into a deformed configuration;
    heating the first portion to a deforming temperature while maintaining the first portion of the tube in the deformed configuration;
    maintaining the first portion of the tube in the deformed configuration at the deforming temperature for a duration of time; and
    cooling the first portion of the tube to a setting temperature after the duration of time has elapsed,
    wherein the first portion of the tube includes a deformed section in which the first and second opposing sidewalls are closer to one another than in another section of the first portion, the deformed section facilitating transitioning between collapse and expansion of the deformed section, and
    wherein the deformed section of the first portion of the tube is configured to:
        collapse as a result of the first and second opposing sidewalls coming into contact and block flow through the tube responsive to an internal pressure within the tube being reduced compared to an ambient atmospheric pressure outside the tube, the internal pressure within the tube being reduced as a result of negative pressure being applied to the tube, and
        expand as a result of the first and second opposing sidewalls coming apart and permit flow of negative pressure from a negative pressure reservoir through the tube responsive to the internal pressure approaching the ambient atmospheric pressure.

2. The vacuum pressure regulator valve of claim 1, wherein the duration of time is at least 3 seconds.

3. The vacuum pressure regulator valve of claim 1, wherein the first portion of the tube is maintained in the deformed configuration during said cooling.

4. The vacuum pressure regulator valve of claim 1, wherein the process further comprises:
    rotating the tube a half turn along a long axis of the tube from a first circumferential position to a second circumferential position; and
    compressing again the first portion of the tube.

5. The vacuum pressure regulator valve of claim 1, wherein the process further comprises:
    compressing a second portion of the tube, wherein the second portion is adjacent to the first portion.

6. The vacuum pressure regulator valve of claim 5, wherein the process further comprises:
    compressing a third portion of the tube, wherein the first portion of the tube is disposed longitudinally between to the second portion of the tube and the third portion of the tube.

7. The vacuum pressure regulator valve of claim 1, wherein the tube is made of a transparent thermoplastic elastomer tubing.

8. The vacuum pressure regulator valve of claim 1, wherein the deforming temperature is between 90° C. and 110° C.

9. The vacuum pressure regulator valve of claim 1, wherein compressing the first and second opposing sidewalls of the first portion of the tube comprises applying a deforming pressure of 3 Bars to the first portion of the tube.

10. The vacuum pressure regulator valve of claim 1, wherein the setting temperature is 80° C.

11. The vacuum pressure regulator valve of claim 1, wherein the process further comprises:
    connecting an inlet at a first end of the tube and an outlet at a second end of the tube opposite the first end, the inlet maintaining the first and second opposing sidewalls open at the first end and the outlet maintaining the first and second opposing sidewalls open at the second end.

12. The vacuum pressure regulator valve of claim 1, wherein the deformed section of the first portion is configured to expand responsive to a pressure differential created by the internal pressure that is negative acting on inner surfaces of the first and second opposing sidewalls and the ambient atmospheric pressure acting on external surfaces of the first and second opposing sidewalls.

13. The vacuum pressure regulator valve of claim 1, wherein the process further comprises forming an inlet opening by inserting a portion of an inlet into a first end of the tube and forming an outlet opening by inserting a portion of an outlet into a second end of the tube opposite the first end, wherein the portion of the inlet inserted into the first end of the tube maintains first and second opposing sidewalls in an open configuration at the first end of the tube, and wherein the portion of the outlet inserted at the second end of the tube maintains the first and second opposing sidewalls in an open configuration at the second end of the tube.

* * * * *